United States Patent
Palushi et al.

(10) Patent No.: US 11,559,673 B2
(45) Date of Patent: Jan. 24, 2023

(54) MULTI-BALLOON INSTRUMENT FOR DILATING EUSTACHIAN TUBE VIA MIDDLE EAR

(71) Applicant: Acclarent, Inc., Irvine, CA (US)

(72) Inventors: Jetmir Palushi, Irvine, CA (US); Fatemeh Akbarian, Rancho Palos Verdes, CA (US)

(73) Assignee: Acclarent, Inc., Irvine, CA (US)

( * ) Notice: Subject to any disclaimer, the term of this patent is extended or adjusted under 35 U.S.C. 154(b) by 348 days.

(21) Appl. No.: 16/402,295

(22) Filed: May 3, 2019

(65) Prior Publication Data

US 2019/0388662 A1 Dec. 26, 2019

Related U.S. Application Data

(60) Provisional application No. 62/688,442, filed on Jun. 22, 2018.

(51) Int. Cl.
*A61M 29/02* (2006.01)
*A61M 25/10* (2013.01)

(52) U.S. Cl.
CPC ..... *A61M 29/02* (2013.01); *A61M 2025/1015* (2013.01); *A61M 2025/1061* (2013.01); *A61M 2029/025* (2013.01); *A61M 2210/0668* (2013.01); *A61M 2210/0675* (2013.01)

(58) Field of Classification Search
CPC ...... A61B 17/24; A61F 11/002; A61F 11/004; A61M 2025/1015; A61M 2025/1061; A61M 2029/025; A61M 2210/0668; A61M 2210/0675; A61M 25/1011; A61M 29/02
See application file for complete search history.

(56) References Cited

U.S. PATENT DOCUMENTS

| | | | |
|---|---|---|---|
| 10,070,993 B2 | 9/2018 | Chan et al. | |
| 2003/0055398 A1 | 3/2003 | Imran | |
| 2008/0051706 A1 | 2/2008 | Hirszowicz et al. | |
| 2010/0152717 A1* | 6/2010 | Keeler | A61B 18/20 606/7 |
| 2010/0274188 A1 | 10/2010 | Chang et al. | |
| 2010/0312101 A1* | 12/2010 | Drontle | A61B 17/24 600/424 |
| 2011/0004057 A1* | 1/2011 | Goldfarb | A61M 29/02 600/106 |
| 2012/0116439 A1* | 5/2012 | Ho | A61F 2/2427 606/194 |
| 2013/0261544 A1 | 10/2013 | Hardin | |

(Continued)

OTHER PUBLICATIONS

International Search Report and Written Opinion dated Dec. 11, 2019 for Application No. PCT/IB2019/055098, 16 pgs.

(Continued)

*Primary Examiner* — Mohamed G Gabr
(74) *Attorney, Agent, or Firm* — Frost Brown Todd LLC

(57) ABSTRACT

A dilation catheter includes a shaft, a distal tip sized and configured to pass through an isthmus of a Eustachian tube (ET), and an expandable element moveable along an exterior of the shaft between a proximal position and a distal position. The expandable element is operable to transition between an unexpanded state in which the expandable element is configured for insertion into the ET via the isthmus, and an expanded state in which the expandable element is configured to dilate the ET.

20 Claims, 13 Drawing Sheets

(56) References Cited

U.S. PATENT DOCUMENTS

| | | | |
|---|---|---|---|
| 2013/0274715 A1 | 10/2013 | Chan et al. | |
| 2014/0275804 A1* | 9/2014 | Kesten | A61F 5/08 |
| | | | 600/249 |
| 2015/0374963 A1 | 12/2015 | Chan et al. | |
| 2016/0067465 A1* | 3/2016 | Gerrans | A61M 29/02 |
| | | | 606/196 |
| 2016/0081857 A1* | 3/2016 | Ha | A61F 11/20 |
| | | | 600/106 |
| 2017/0056629 A1 | 3/2017 | Agah et al. | |
| 2018/0369548 A1* | 12/2018 | Eaton | A61B 17/12181 |

OTHER PUBLICATIONS

U.S. Appl. No. 62/688,442, entitled "Multi-Balloon Instrument for Dilating Eustachian Tube Via Middle Ear," filed Jun. 22, 2018.

* cited by examiner

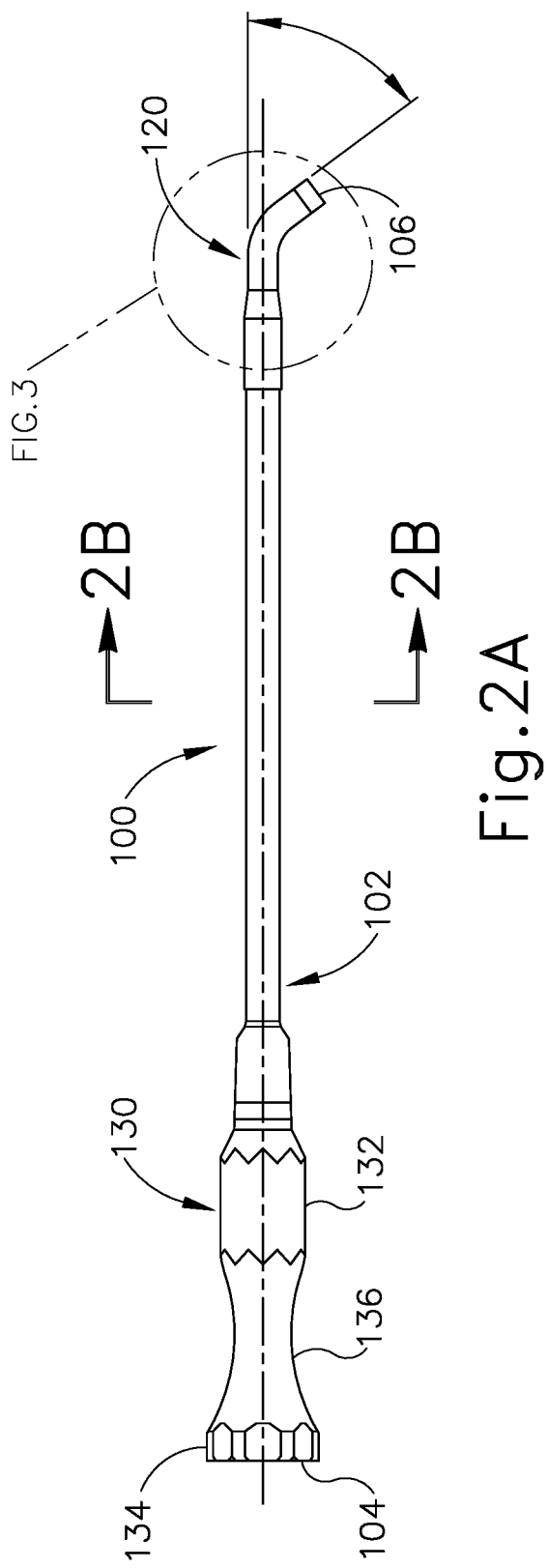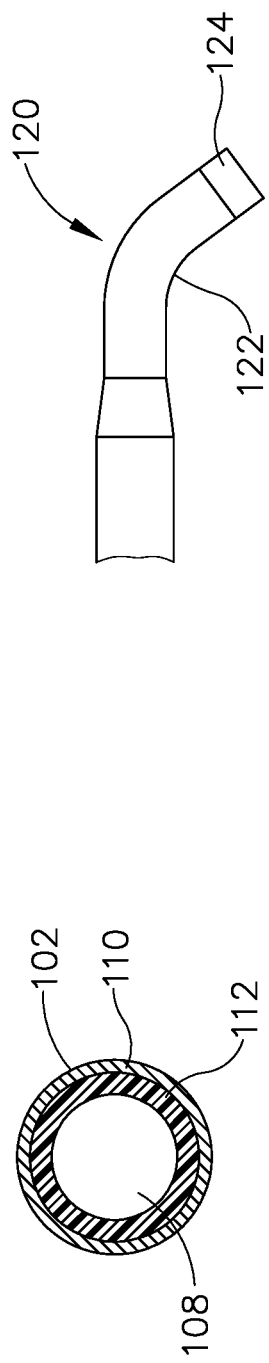

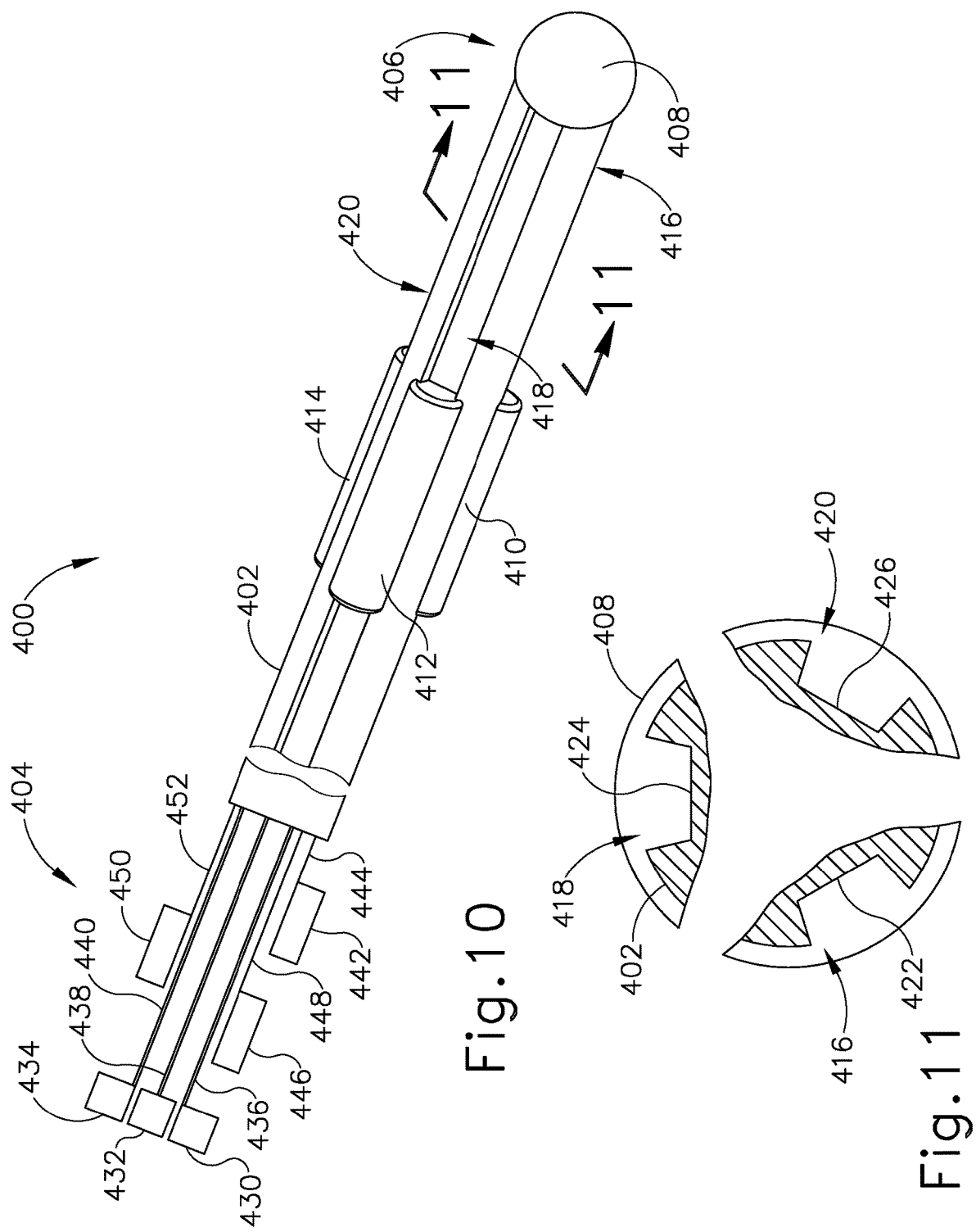

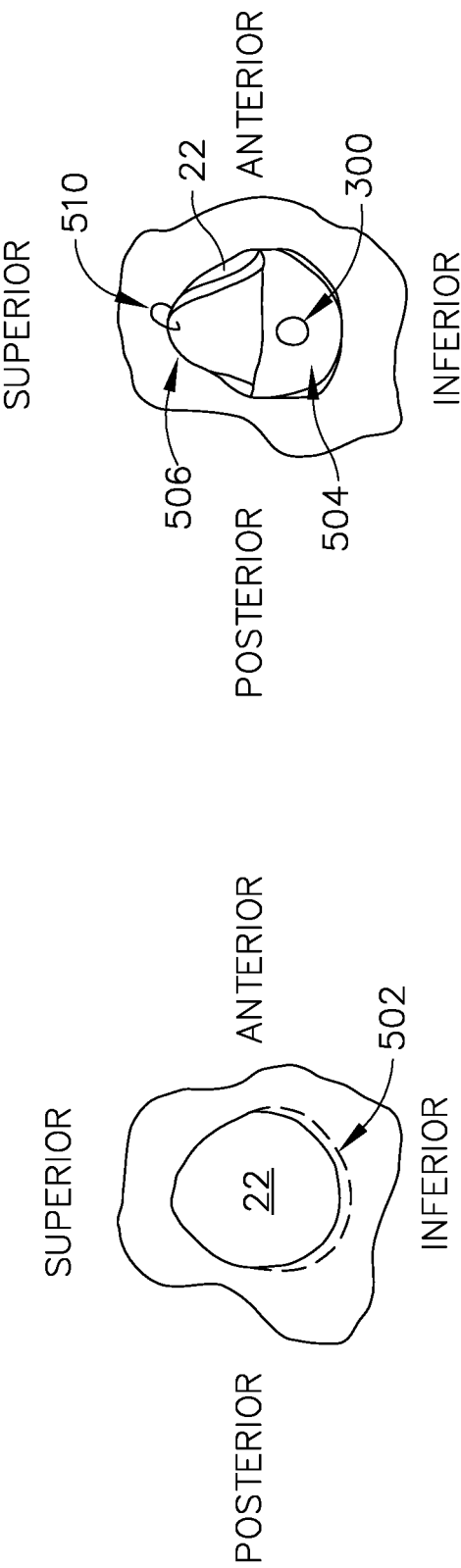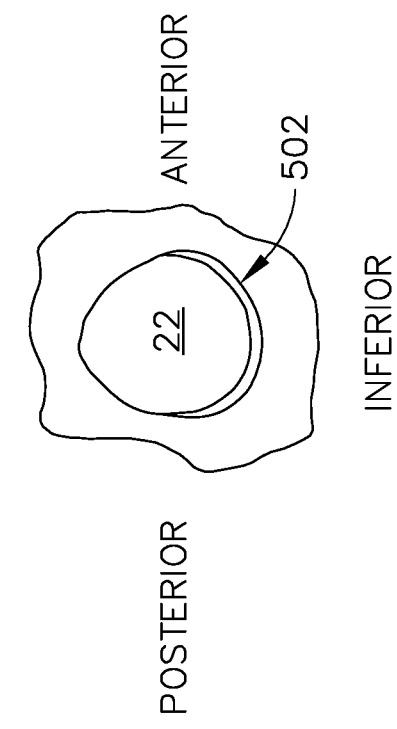

MULTI-BALLOON INSTRUMENT FOR DILATING EUSTACHIAN TUBE VIA MIDDLE EAR

PRIORITY

This application claims priority to U.S. Provisional Patent App. No. 62/688,442, entitled "Multi-Balloon Instrument for Dilating Eustachian Tube Via Middle Ear," filed Jun. 22, 2018, the disclosure of which is incorporated by reference herein.

BACKGROUND

Referring to FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This occurs frequently in children in connection with an upper respiratory infection and accounts for the hearing impairment associated with this condition.

A lining membrane (mucous membrane) of the middle ear (14) and ET (26) is connected with, and is the same as, the membrane of the nose (42), sinuses (44) and throat (32). Infection of these areas results in mucous membrane swelling which in turn may result in obstruction of the ET (26). This is referred to as serous otitis media, which as discussed above is essentially a collection of fluid in the middle ear (14). Serous otitis media can be acute or chronic, and may be the result of blockage of the pharyngeal ostium (28) of the ET (26), which leads to the accumulation of fluid in the middle ear (14). In the presence of bacteria, this fluid may become infected, leading to an acute suppurative otitis media (infected or abscessed middle ear). When infection does not develop, the fluid remains until the ET (26) again begins to function normally, at which time the fluid is absorbed or drains down the tube into the throat (32) through the ET (26) pharyngeal ostium (28).

Chronic serous otitis media may result from longstanding ET blockage, or from thickening of the fluid so that it cannot be absorbed or drained down the ET (26). This chronic condition may lead to hearing impairment. There may be recurrent ear pain, especially when the individual catches a cold. Fortunately, serous otitis media may persist for many years without producing any permanent damage to the middle ear mechanism. The presence of fluid in the middle ear (14), however, makes it very susceptible to recurrent acute infections. These recurrent infections may result in middle ear damage.

When the ET (26) contains a build-up of fluid, a number of things may occur. First, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Treatment of this condition with antihistamines and decongestants can take many weeks to be fully effective. Finally, the fluid can become infected, which can lead to pain, illness, and temporary hearing loss. If the inner ear (14) is affected, the patient may feel a spinning or turning sensation (vertigo). The infection may be treated with antibiotics.

However, even if antihistamines, decongestants, and antibiotics are used to treat an infection or other cause of fluid build-up in the middle ear (14), these treatments may not immediately resolve the pain and discomfort caused by the buildup of fluid in the middle ear (14). The most immediate relief may be felt by the patient if the fluid can be removed from the ET (26).

Antibiotic treatment of middle ear infections may result in normal middle ear function within three to four weeks. During the healing period, the patient can experience varying degrees of ear pressure, popping, clicking and fluctuation of hearing, occasionally with shooting pain in the ear. Resolution of the infection may leave the patient with uninfected fluid in the middle ear (14), localized in the ET (26).

Fluid build-up caused by these types of infections may be treated surgically. The primary objective of surgical treatment of chronic serous otitis media may be to reestablish ventilation of the middle ear, keeping the hearing at a normal level and preventing recurrent infection that might damage the eardrum membrane and middle ear bones. One method to opening the ET (26) includes the "Valsalva" maneuver, accomplished by forcibly blowing air into the middle ear (14) while holding the nose, often called popping the ear. This method may be effective for opening the ET (26) but it may not clear the accumulated fluid from the middle ear (14) and is essentially a temporary fix when fluid is present in the middle ear (14).

Methods for treating the middle ear (14) and the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, now abandoned, the disclosure of which is incorporated by reference herein; and U.S. Patent Pub. No. 2015/0374963, entitled "Vent Cap for a Eustachian Tube Dilation System," published on Dec. 31, 2015, issued as U.S. Pat. No. 10,350,396 on Jul. 16, 2019, the disclosure of which is incorporated by reference herein. As described in those references, functioning of the ET (26) may be improved by dilating the ET (26) with an expandable dilator instrument.

While a variety of surgical instruments have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2A depicts a side elevational view of an exemplary guide catheter;

FIG. 2B depicts a cross-sectional view of the guide catheter of FIG. 2A, taken along line 2B-2B in FIG. 2A;

FIG. 3 depicts an enlarged elevational view of the distal end of the guide catheter of FIG. 2A;

FIG. 10 depicts a perspective view of an exemplary balloon dilation catheter having first, second, and third balloons shown deflated and in proximal positions, with a proximal end portion of the dilation catheter shown schematically;

FIG. 11 depicts a cross-sectional view of the balloon dilation catheter of FIG. 10, taken along line 11-11 in FIG. 10, showing longitudinal grooves of the dilation catheter;

FIG. 14A depicts a schematic view of the tympanic membrane of FIG. 13A, viewing medially from the ear canal, before the step shown in FIG. 13A;

FIG. 14B depicts a schematic view of the tympanic membrane of FIG. 13A, viewing medially from the ear canal, showing tissue surrounding the tympanic membrane having been incised and the tympanic membrane having been folded upwardly to provide access to the middle ear, with the balloon dilation catheter of FIG. 7 having been inserted into the middle ear to perform the steps shown in FIGS. 13A-13C; and FIG. 14C depicts a schematic view of the tympanic membrane of FIG. 13A, viewing medially from the ear canal, showing the tissue surrounding the tympanic membrane and the tympanic membrane replaced to their original positions using a fixation method, after completion of the steps shown in FIGS. 13A-13C.

Figure 1:
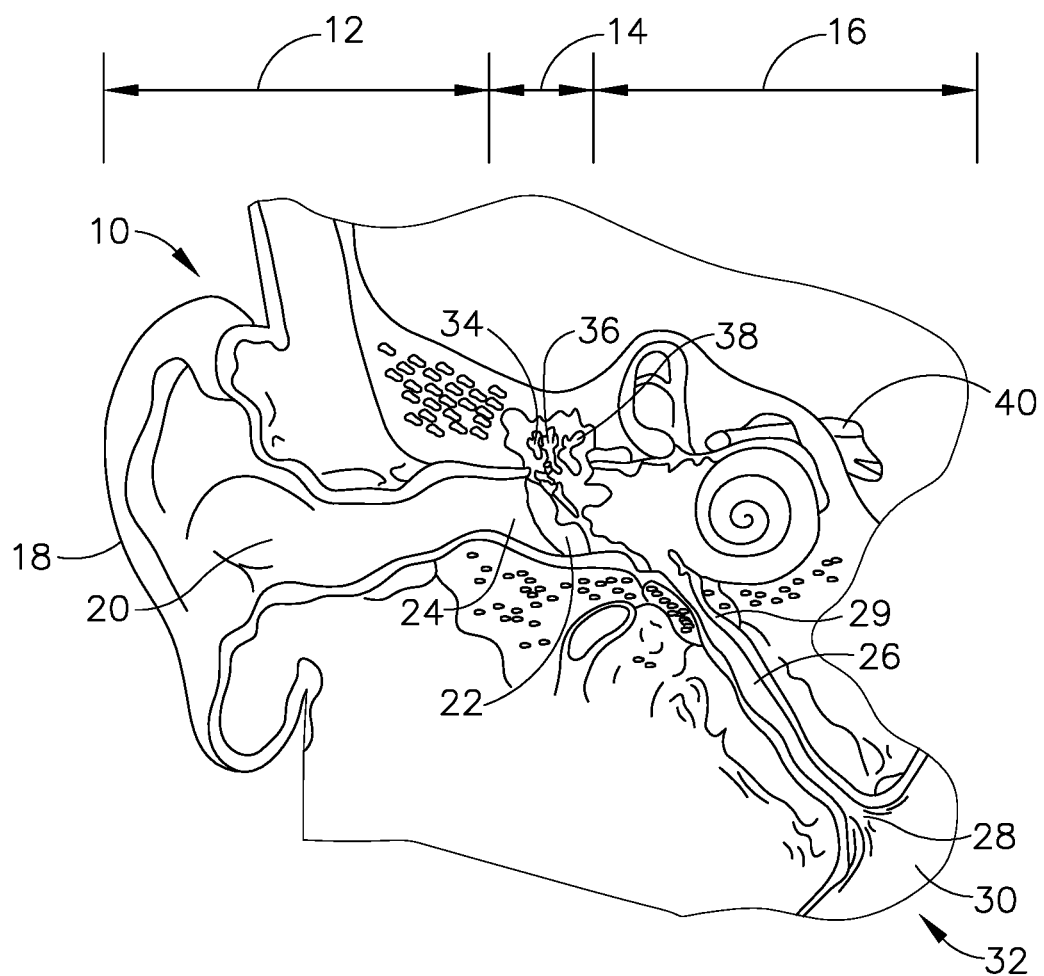
FIG. 1 depicts a cross-sectional view of a patient's head, showing the inner ear, the middle ear, the outer ear, and the Eustachian tube connecting the middle ear with the nasopharynx region of the throat.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Eustachian Tube Dilation Catheter System

One example of a treatment that may be performed to treat an ET (26) that does not provide sufficient communication between the middle ear (14) and the pharyngeal ostium (28) includes accessing and dilating the ET (26) using a guide catheter (100) and a balloon dilation catheter (200), examples of which are shown in FIGS. 2A-5. Guide catheter (100) of the present example includes an elongate tubular shaft (102) that has a proximal end (104), a distal end (106) and a lumen (108) therebetween. The guide catheter (100) may have any suitable length, diameter, angle of bend, and location of the bend along the length of the catheter (100), to facilitate accessing an ET (26) opening, such as the pharyngeal ostium (28). In some examples, the guide catheter (100) may have a length between about 8 cm and about 20 cm, or more particularly between about 10 cm and about 15 cm, or more particularly about 11 cm.

FIG. 2B is a cross-sectional view of the elongate tubular shaft (102) of guide catheter (100). As can be seen, shaft (102) has an outer shaft tube (110), an inner shaft tube (112) and a lumen (108). The outer shaft tube (110) may be constructed of a stiff material such as stainless steel and the inner shaft tube (112) may be constructed of a more flexible material such as a polymeric material including but not limited to nylon and further including a PTFE liner. The lumen (108) has a diameter of between about 2 mm and 3 mm, or more particularly between about 2.5 mm and about 2.6 mm, such that the balloon dilation catheter (200) can be easily inserted into the lumen (108) for dilation of the ET (26). The combination of guide catheter (100) and balloon catheter (200) may a compact system that is designed for a one-handed procedure. By "compact," it is intended that the length of the guide catheter shaft that is distal of the bend in the guide catheter is between about 0.5 and 2.0 about cm, in some versions between about 1 and about 2 cm, and in some versions about 1 cm. The compactness may help reduce interference with other instruments, such as an endoscope that may be used to help in visualizing the positioning of the system, as described below.

The distal portion (120) of guide catheter (100) is shown in an enlarged view in FIG. 3. The distal portion (120) of the guide catheter (100) may have a bend (122) with an angle between about 45 degrees and about 65 degrees, and more preferably between about 50 degrees and about 60 degrees, and particularly about 55 degrees, to facilitate access into the ET (26) via the pharyngeal ostium (28). The distal portion (120) of the guide catheter (100) is made of a transparent material such as a polymer including but not limited to nylon and PTFE such that balloon dilation catheter (200) is visible within the distal portion (120) and such that distal portion (120) is more flexible than the elongate shaft (102). The distal tip (124) of the distal portion (120) of the guide catheter (100) is made of PEBAX® (polyether block amide) such that it provides for atraumatic access to the ET (26), and may contain 20% barium sulfate or other similar radiopaque materials for visualizable access.

Referring again to FIG. 2A, the proximal portion (130) of guide catheter (100) includes a proximal hub (132) to aid in insertion of balloon catheter (200) into the ET (26). The hub (132) has a larger diameter proximal end (134) and a smaller diameter middle section (136) to facilitate stabilization of the guide catheter (100) in the nose, rotation of the guide catheter (100), and insertion of the balloon catheter (200) as will be described in further detail below. The hub (132) is ergonomically designed for insertion, location, and rotation through slight manipulations with one hand.

Figure 4A:
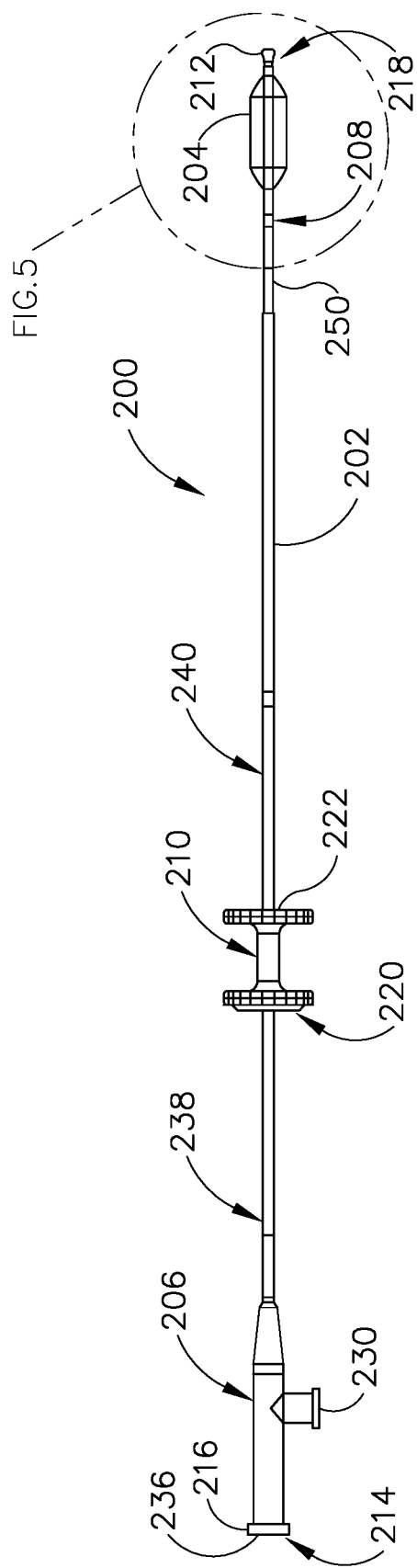
FIG. 4A depicts a side elevational view of an exemplary balloon dilation catheter that may be used with the guide catheter of FIG. 2A.
Figure 4B:
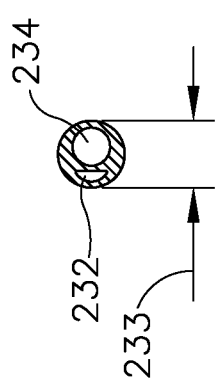
FIG. 4B depicts a cross-sectional view of the balloon dilation catheter of FIG. 4A, taken along line 4B-4B in FIG. 5.
Figure 5:
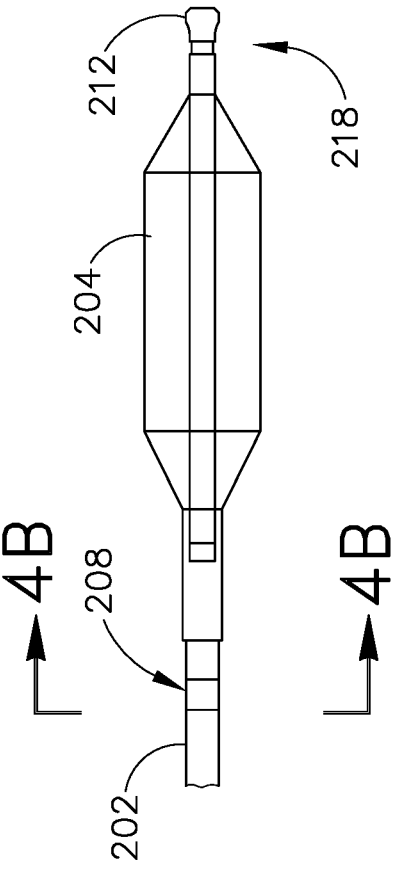
FIG. 5 depicts an enlarged elevational view of the distal end of the balloon dilation catheter of FIG. 4A.

Balloon dilation catheter (200) of the present example is shown in FIG. 4A. Balloon dilation catheter (200) of the present example generally includes an elongate shaft (202) having a proximal end (214) and a distal end (218). The balloon dilation catheter (200) further includes a balloon (204) longitudinally fixed at the distal end (218) of the elongate shaft (202). The balloon (204) may be a polymer balloon (compliant, semi-compliant, or non-compliant). In some versions, the balloon (204) comprises a suitable non-compliant material such as but not limited to polyethylene terepthalate (PET), PEBAX® (polyether block amide), nylon or the like. The balloon catheter (200) may include any size of balloon including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm). The balloon dilation catheter (200) generally includes a proximally located connection (230) for inflating/activating the balloon (204) by communicating a pressurized medium (e.g., saline) to balloon (204).

Figure 6A:
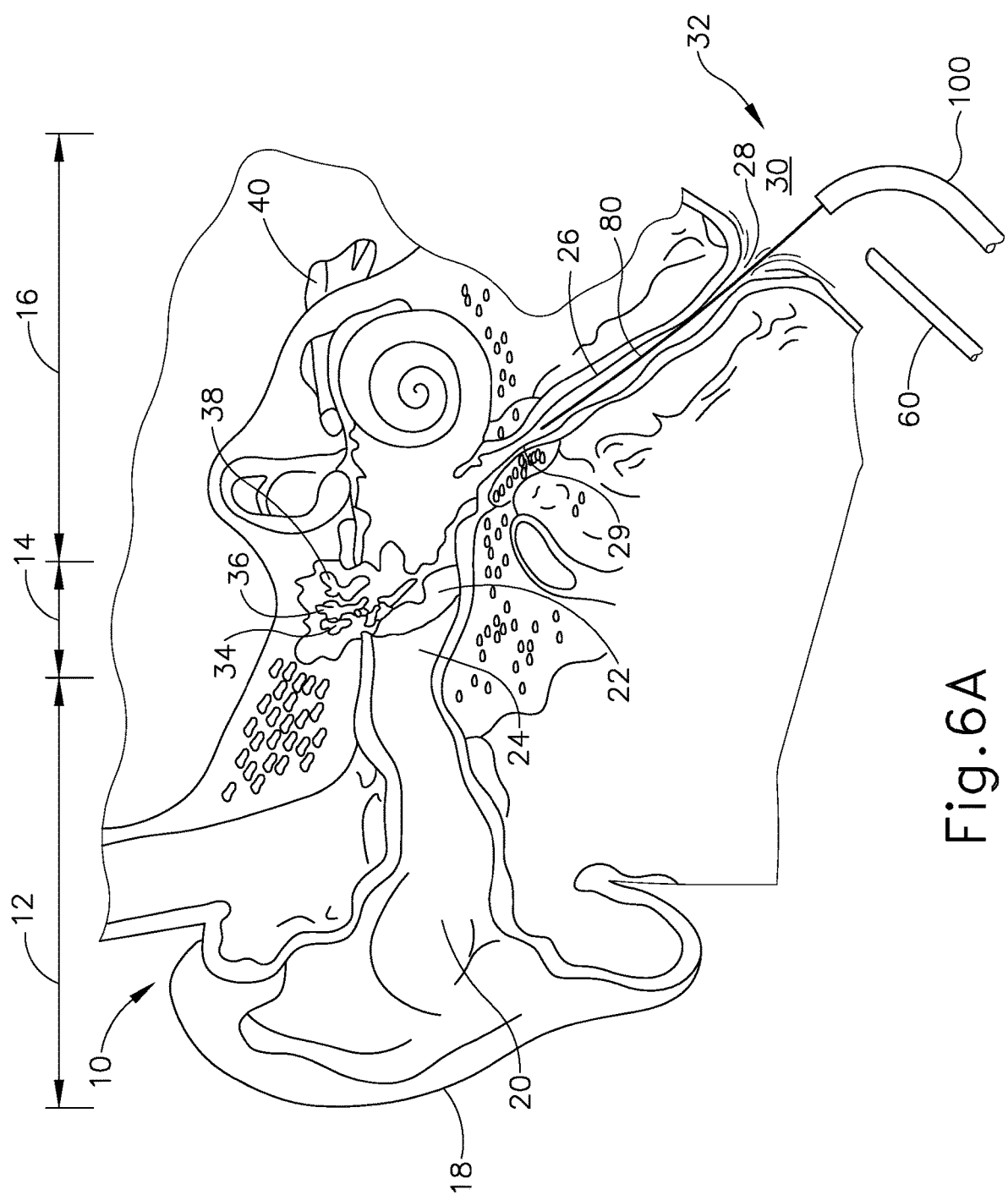
FIG. 6A depicts a cross-sectional view of a patient's head, showing the guide catheter of FIG. 2A, a guidewire, and an endoscope being positioned in relation to the patient's Eustachian tube via the throat.
Figure 6B:
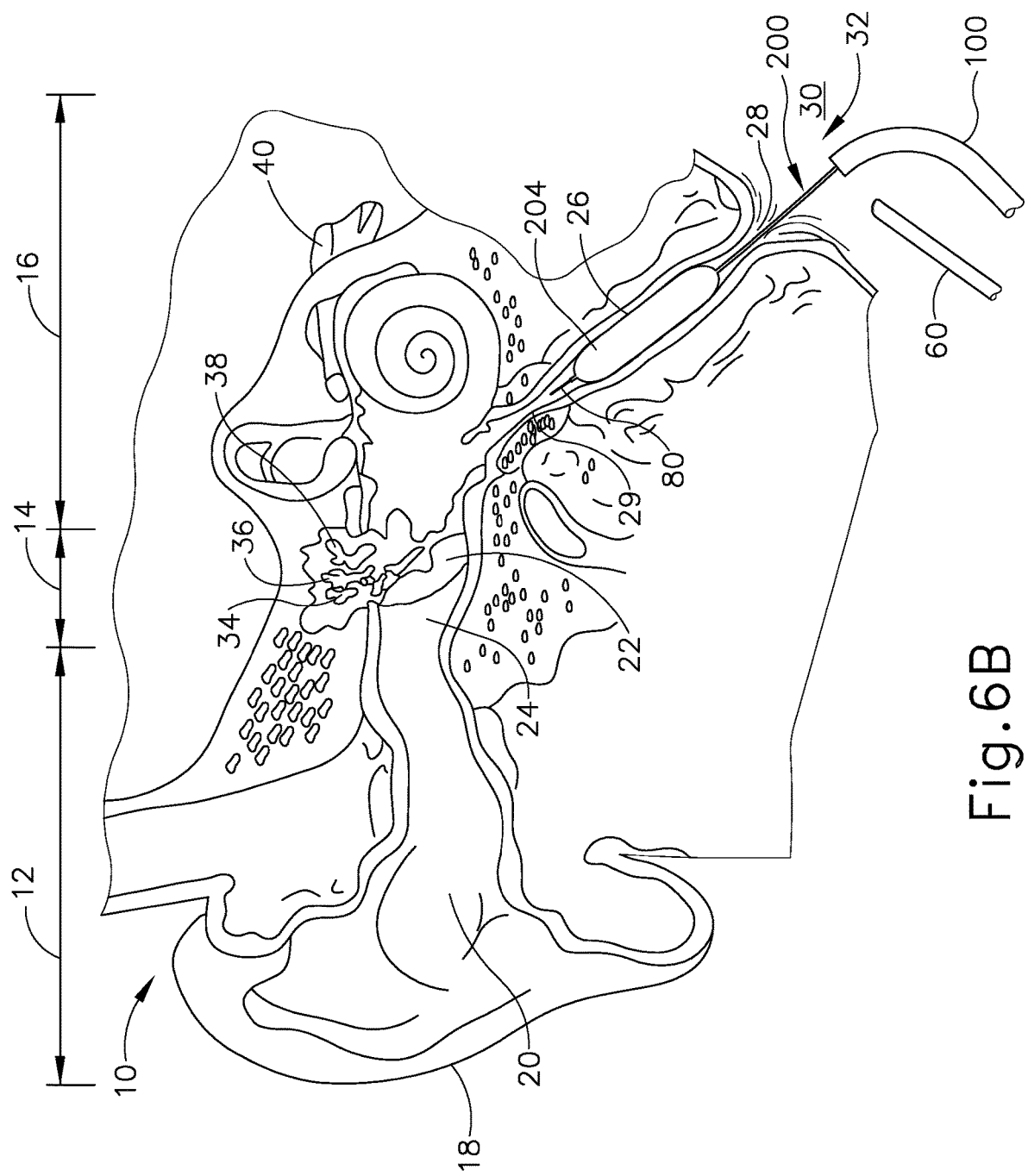
FIG. 6B depicts a cross-sectional view of the patient's head of FIG. 6A, showing the balloon dilation catheter of FIG. 4A inserted into the Eustachian tube and subsequently expanded to dilate the Eustachian tube.

Balloon (204) may be expanded to dilate the ET (26) after balloon (204) is placed in a desirable location in the ET (26), as shown in FIGS. 6A-6B and described in greater detail below. For example, the opening area of the ET (26) includes a pharyngeal ostium (28), and dilation catheter (200) may be advanced to position the balloon in the pharyngeal ostium (28). An endoscope (60) may be used to assist in positioning the dilation catheter (200). Endoscope (60) may be advanced through the nasal passage to view the dilation catheter (200). A marker (208) on a shaft of the dilation catheter (200) can be viewed from endoscope (60) to approximate a location of the balloon (204) relative to the opening of the ET (26) (e.g., pharyngeal ostium (28)) based on a distance of the marker (208) from a proximal end of the balloon (204). Accordingly, dilation catheter (200) can be moved to place marker (208) in a desirable location before expansion of the balloon (204) in the ET (26).

Balloon dilation catheter (200) further includes an actuator (210). Actuator (210) has a proximal side 220 and a distal side (222). In the example shown in FIG. 4A, actuator (210) is secured by an adhesive to elongate shaft (202). The portion (240) of elongate shaft (202) that is distal of actuator (210) is sufficiently stiff to be guided through the nasal cavity and into the ET (26) and is constructed of stainless steel and preferably includes a stainless steel hypotube. The portion (238) of elongate shaft (202) that is proximal of actuator (210) and the portion (250) that is distal to portion (240) is more flexible than the portion (240) and is constructed of a polymeric material including but not limited to PEBAX® (polyether block amide). In this way, proximal portion (238) of elongate shaft (202) will not interfere with the endoscope (60) described above as it is advanced through the nasal passage, such that the dilation catheter (200) can be easily viewed. The actuator (210) allows for easy, ergonomic one-handed advancement of dilation catheter (200) through guide catheter (100) and into the ET (26). Actuator (210) may be used to advance or retract in alternative ways including but not limited to use of the thumb, the index finger, or a combination of fingers (e.g., the index and middle fingers) or the thumb and the index or middle finger.

The distal end (218) of balloon catheter (200) further includes a tip (212) and a flexible shaft portion (250) that is constructed of a polymeric material including but not limited to PEBAX® (polyether block amide) that extends from the distal end of the elongate shaft (202) to the proximal end of balloon (204). In the example shown in FIG. 4A, tip (212) is a bulbous polymeric blueberry-shaped, atraumatic tip and is about 1.5 mm to about 2 mm in length, with an outer diameter of between about 2 mm and about 3 mm. The smoothness and roundness of tip (212) facilitates advancement of the balloon catheter (200) by helping it glide smoothly through the ET (26). Tip (212) further acts as a safety stop. The isthmus (29) of the ET (26), shown in FIG. 1 is approximately 1 mm in diameter. The tip (212) diameter is larger than the outer diameter (233) of the elongate shaft (202) shown in cross-section in FIG. 4B such that the tip (212) size will prevent the balloon catheter (200) from passing through the isthmus (29) into the middle ear (14).

After balloon (204) is positioned within the ET (26) and inflated to an expanded state (e.g., as shown in FIG. 6B), balloon (204) may be held in location while in an expanded state for an extended period of time (e.g. several seconds or minutes). The balloon catheter (200) may also deliver a substance to the ET (26), such as one or more of the therapeutic or diagnostic agents described herein. Balloon (204) may also carry an expandable stent for delivery into the ET (26) upon expansion of balloon (204). Balloon dilation catheter (200) and guide catheter (100) may be removed from the patient after balloon (204) has been deflated/unexpanded. The ET (26) will resume functioning, normally opening and closing to equalize atmospheric pressure in the middle ear (14) and protect the middle ear (14) from unwanted pressure fluctuations and loud sounds.

II. Exemplary Eustachian Tube Dilation Catheters Having Multiple Expandable Elements In some instances, it may be difficult or impossible to access the ET (26) by inserting instruments through the nostril, into the oro-nasal cavity, and through the pharyngeal ostium, as shown in FIGS. 6A-6B described above. This may be due to the anatomical constraints of a patient or, in some instances, to the limitations of a particular practitioner's skill set. Therefore, in some instances, it may be more efficacious to access the ET (26) through the tympanic membrane (22) and the middle ear (14). However, due to the sensitive nature of the tympanic membrane (22) and middle ear structures, it may be advantageous to access the ET (26) in a manner that preserves the integrity of the ET (26) or minimizes trauma to the ET (26). Moreover, because this approach of accessing the ET (26) requires a practitioner to direct instruments through the isthmus (29), care must be taken due to the small size and sensitive nature of the isthmus (29) and adjacent structures of the inner ear (16).

The exemplary alternative dilation catheters (300, 400) described below enable a practitioner to safely access the ET (26) via the middle ear (14) while still being operable to provide sufficient dilation of the ET (26) once positioned.

A. Exemplary Eustachian Tube Dilation Catheter Having Two Balloons

Figure 7:
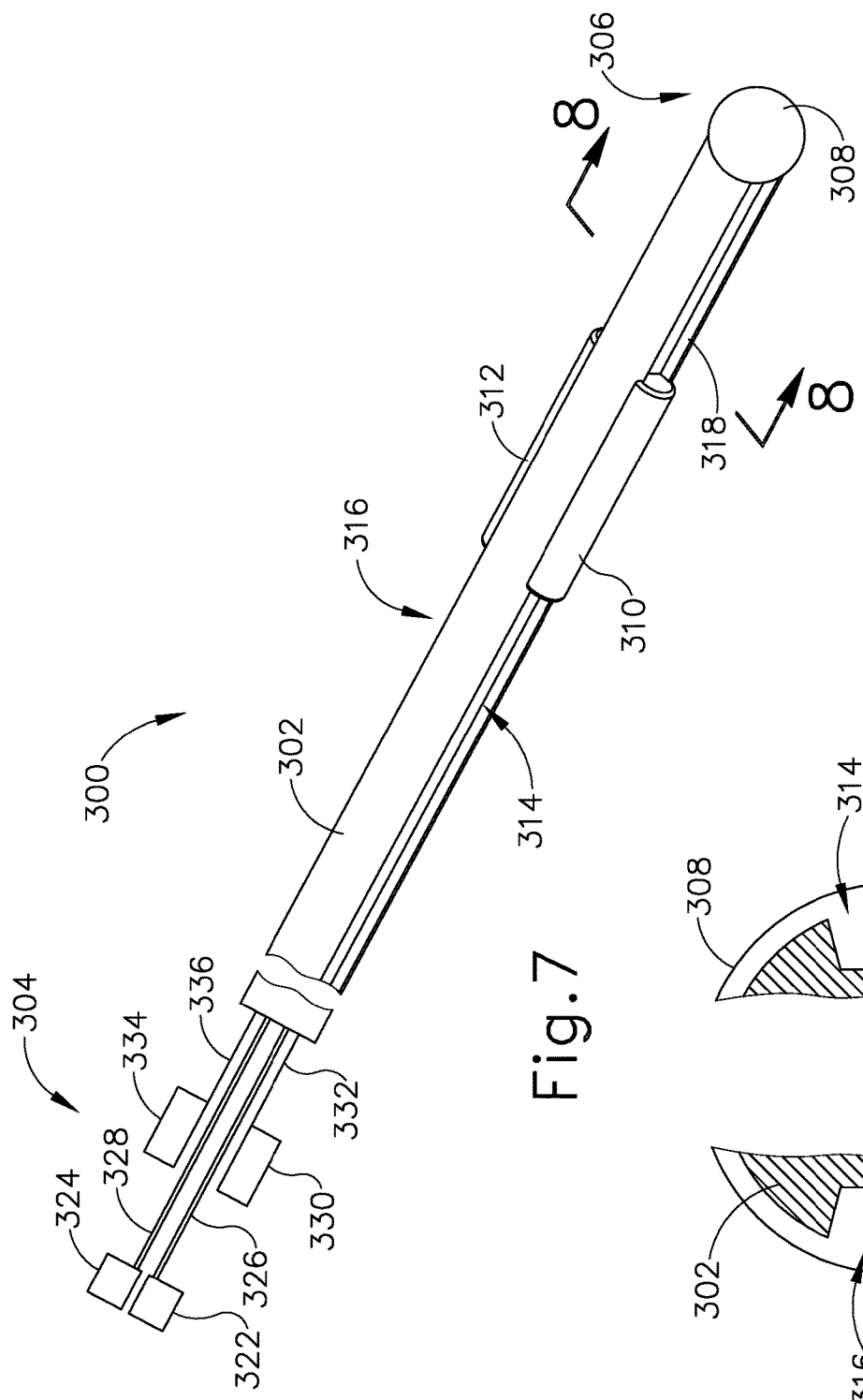
FIG. 7 depicts a perspective view of an exemplary balloon dilation catheter having first and second balloons shown deflated and in proximal positions, with a proximal end portion of the dilation catheter shown schematically.

FIG. 7 shows an exemplary dilation catheter (300) that is sized and configured to access the ET (26) through the tympanic membrane (22), the middle ear (14), and the isthmus (29), and which is suitable for use with guide catheter (100) described above. Dilation catheter (300) includes an elongate shaft (302) extending between a proximal end portion (304) (shown schematically) and a distal end (306), and an atraumatic tip (308) arranged at distal end (306). Atraumatic tip (308) of the present example is generally rounded in shape and is suitably sized to pass through the isthmus (29) and into the ET (26), as described in greater detail below. Shaft (302) and tip (308) may be formed of a variety of suitable materials, such as a flexible polymeric material such as PEBAX® (polyether block amide), for instance.

Dilation catheter (300) further includes a first expandable element in the form of a first balloon (310), and a second expandable element in the form of a second balloon (312). Each balloon (310, 312) of the present example is in the form of a semi-compliant balloon configured to generally conform to the outer shape of shaft (302) when deflated, and to assume a predefined geometry and maximum size and when inflated. In other examples, one or both of balloons (310, 312) may be fully compliant or non-compliant. Each balloon (310, 312) may be formed of a suitable polymeric material such as a polyethylene terepthalate (PET), nylon, or the like. Each balloon (310, 312) may include a different reacting agent such a drug or other chemical. When such a reacting agent is infused through the pores outside of the balloon (310, 312), it can create a reaction at the anatomical targeted tissue that might have been impossible otherwise.

Figure 9A:
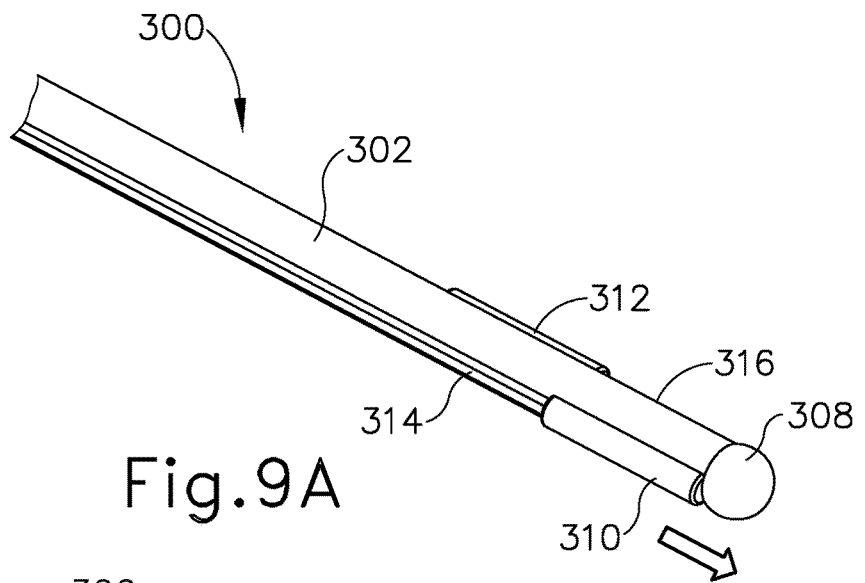
FIG. 9A depicts a perspective view of a distal portion of the balloon dilation catheter of FIG. 7, showing the first balloon in a distal position and the second balloon in a proximal position, with both balloons in a deflated state.
Figure 9B:
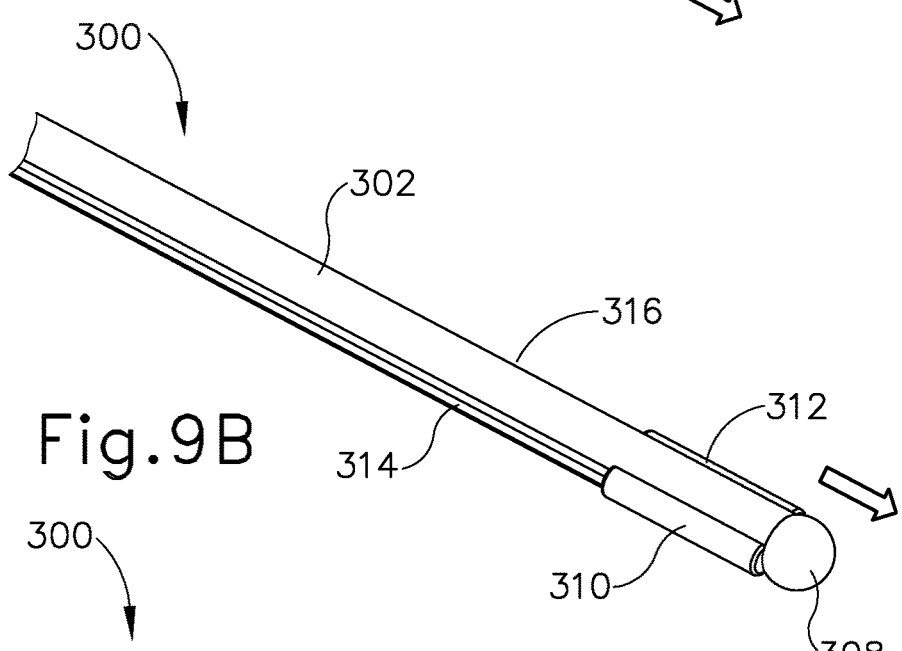
FIG. 9B depicts a perspective view of the distal portion of the balloon dilation catheter of FIG. 7, showing both balloons in their distal positions and deflated.
Figure 9C:
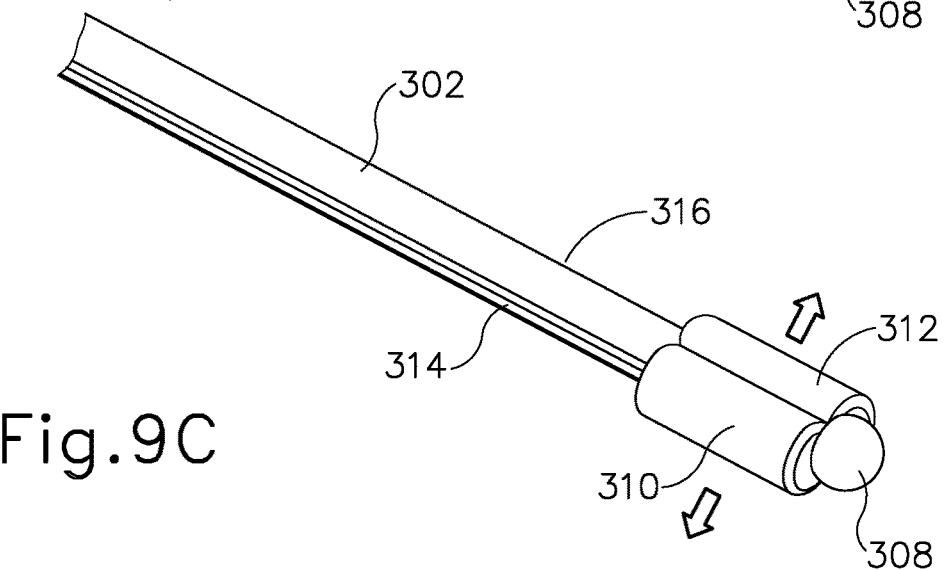
FIG. 9C depicts a perspective view of the distal portion of the balloon dilation catheter of FIG. 7, showing both balloons in an inflated state.

Balloons (310, 312) of the present example are suitably sized and mounted to shaft (302) to provide dilation catheter (300) with a maximum outer diameter of less than or equal to approximately 1 millimeter when balloons (310, 312) are deflated, as shown in FIGS. 7 and 9A-9B. Balloons (310, 312) of the present example are further configured to cooperate to provide dilation catheter (300) with a maximum outer diameter of approximately 6 millimeters or greater when balloons (310, 312) are fully inflated, as shown in FIG. 9C. In at least some applications, a maximum outer diameter of approximately 6 millimeters provides sufficient dilation of a patient's ET (26) during an ET dilation procedure. It will be appreciated, however, that balloons (310, 312) may be suitably configured to assume other maximum sizes for use in other applications and dilation procedures. Each balloon (310, 312) of the present example may have a working length of approximately 12 millimeters to approximately 24 millimeters. In other examples, each balloon (310, 312) may have a working length of approximately 20 millimeters to approximately 40 millimeters.

Figure 8:
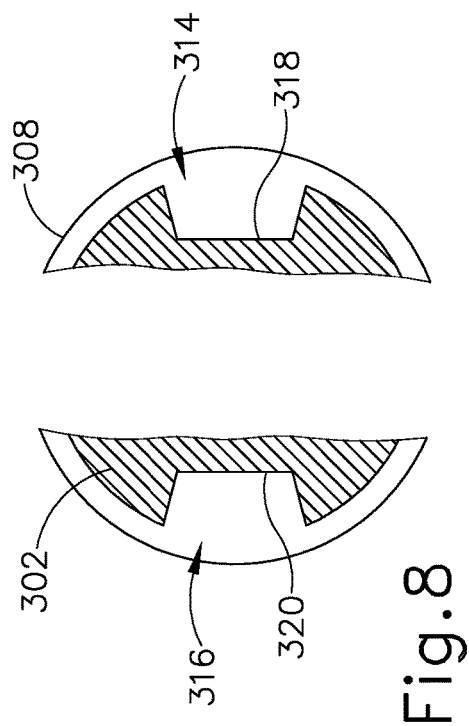
FIG. 8 depicts a cross-sectional view of the balloon dilation catheter of FIG. 7, taken along line 8-8 in FIG. 7, showing longitudinal grooves of the dilation catheter.

Balloons (310, 312) are slidably coupled with an exterior of shaft (302) and are configured to translate proximally and distally along shaft (302) independently of one another, as described in greater detail below. In the present example, shaft (302) includes a first elongate balloon support member in the form of a first rail (314) extending longitudinally along the exterior of a first side of shaft (302). Shaft (302) further includes a second elongate balloon support member in the form of a second rail (316) extending longitudinally along the exterior of a second side of shaft (302). First balloon (310) is configured to translate proximally and distally along first rail (314), and second balloon (312) is configured to translate proximally and distally along second rail (316). In this manner, first and second balloons (310, 312) translate along respective longitudinal paths that are laterally offset from the central longitudinal axis of shaft (302). Rails (314, 316) of the present example are diametrically opposed from one another about the longitudinal axis of shaft (302) such that balloons (310, 312) remain opposed from one another during use. Alternative arrangements of balloon support members may be provided in other examples. As seen in FIG. 8, each rail (314, 316) is defined by a respective longitudinal groove (318, 320) formed in a respective side of shaft (302). This configuration enables each balloon (310, 312) to at least partially collapse within the respective groove (318, 320) when in an unexpanded state so as to minimize the outer diameter of dilation catheter (300) during placement within and withdrawal from a patient, as described in greater detail below.

As shown schematically in FIG. 7, proximal end portion (304) of dilation catheter (300) provides a first inflation port (322) and a second inflation port (324), each of which may be similar to inflation port (230) described above. First inflation port (322) fluidly communicates with first balloon (310) via a first inflation lumen structure (326) that defines a first inflation lumen (not shown). Second inflation port (324) fluidly communicates with second balloon (312) via a second inflation lumen structure (328) that defines a second inflation lumen (not shown). Each inflation lumen structure (326, 328) extends longitudinally through an interior of shaft (302) and is configured to communicate a pressurized medium (e.g., saline) to the interior of the respective balloon (310, 312) while permitting translation of the balloon (310, 312) relative to shaft (302). In some examples, each inflation lumen structure (326, 328) may comprise a conduit or other structure formed separately from shaft (302). In other examples, at least a portion of each inflation lumen structure (326, 328) may be defined by an interior portion of shaft (302). In such examples, one or more portions of each inflation lumen structure (326, 328) may be operable to translate with the respective balloon (310, 312) relative to shaft (302) while maintaining fluid communication between the respective balloon (310, 312) and the respective inflation port (322, 324). For instance, in some examples each inflation lumen structure (326, 328) may be defined at least in part by a flexible conduit configured to assume a length sufficient to provide for a distal-most position of the respective balloon (310, 312), as well as the proximal-most position. In other examples, each inflation lumen structure (326, 328) may include two or more portions operable to move (e.g., translate) relative to one another to assume a length suitable to provide for the distal-most position of the respective balloon (310, 312), as well as the proximal-most position.

In the present example, first inflation port (322) and the first inflation lumen (not shown) are fluidically isolated from second inflation port (324) and the second inflation lumen (not shown) so that first balloon (310) and second balloon (312) may be inflated and deflated independently of one another. In other examples, first and second balloons (310, 312) may be in communication with a single inflation port operable to provide for simultaneous inflation and deflation of first and second balloons (310, 312) together in response to a single inflation input. Various other suitable arrangements of inflation ports (322, 324) and inflation lumen structures (326, 328) will be apparent to persons skilled in the art in view of the teachings herein.

As also shown schematically in FIG. 7, proximal end portion (304) of dilation catheter (300) further includes a first balloon actuator (330) operable to actuate first balloon (310) proximally and distally along first rail (314) via a first linkage (332), and a second balloon actuator (334) operable to actuate second balloon (312) proximally and distally along second rail (316) via a second linkage (336). First and second actuators (330, 334) may be activated by a user independently so as to actuate first balloon (310) and second balloon (312) independently of one another. In some examples, each linkage (332, 336) may be coupled directly with a portion of the respective inflation lumen structure (326, 328) such that at least a portion of the lumen structure (326, 328) is translatably driven by the respective actuator (330, 334) to actuate the respective balloon (310, 312). In other examples, each linkage (332, 336) may be coupled with the respective balloon (310, 312) independently of the respective inflation lumen structure (326, 328). Actuators (330, 334) may be in the form of knobs, tabs, rotary dials, or various other structures suitable for engagement by a user to provide manual actuation of balloons (310, 312). In other examples, actuators (330, 334) may comprise motors configured to provide powered actuation of balloons (310, 312).

As described above, each balloon (310, 312) is configured to translate independently along its respective rail (314, 316) between a proximal position and a distal position, in response to user input provided via the respective balloon actuator (330, 334). FIG. 7 shows balloons (310, 312) deflated and in exemplary proximal positions in which balloons (310, 312) are spaced proximally from distal end (306). FIG. 9A shows first balloon (310) in a distal position while second balloon (312) remains in a proximal position. FIG. 9B shows both balloons (310, 312) in distal positions, in which a distal end of each balloon confronts a proximal surface of distal tip (308) of dilation catheter (300). In some examples, the distal end of each balloon (310, 312) may abut the proximal surface of distal tip (308) when the balloon (310, 312) reaches its distal position, such that tip (308) functions as a balloon stop element. In other examples, a balloon stop element may be provided by each rail (314, 316). As shown in FIG. 9C, after being advanced to their distal positions, balloons (310, 312) may be inflated to dilate an anatomical passageway in which balloons (310, 312) are positioned, such as the ET (26) of a patient.

As described above, balloons (310, 312) may be inflated in response to independent inputs provided by a user, or alternatively in response to a single input provided by the user. Balloons (310, 312) of the present example are suitably sized and arranged to provide dilation catheter (300) with a maximum outer diameter of at least 6 millimeters when balloons (310, 312) are inflated in their distal positions, to provide sufficient dilation of the ET (26) of a patient. When deflated, balloons (310, 312) are configured to provide dilation catheter (300) with a maximum outer diameter of less than or equal to approximately 1 millimeter. As shown in FIG. 9C, balloons (310, 312) of the present example are diametrically opposed from one another about the longitudinal axis of shaft (302) so as to define the maximum outer diameter in a first lateral direction transverse to the longitudinal axis, and to further define a smaller, second diameter in a second lateral direction transverse to the first lateral direction. Detailed steps of an exemplary procedure for dilating the ET (26) of a patient with dilation catheter (300) are described in greater detail below in connection with FIGS. 13A-13C.

While dilation catheter (300) is shown and described above as having two expandable elements in the form of first and second balloons (310, 312), dilation catheter (300) may be provided with three or more expandable elements in other examples, for instance as described below in connection with the alternative configuration shown in FIGS. 10-12C.

B. Exemplary Eustachian Tube Dilation Catheter Having Three Balloons

FIG. 9 shows another exemplary dilation catheter (400) that is sized and configured to access the ET (26) through the tympanic membrane (22), the middle ear (14), and the isthmus (29), and which is suitable for use with guide catheter (100) described above. Dilation catheter (400) is substantially similar to dilation catheter (300) described above, except as otherwise described below. Similar to dilation catheter (300), dilation catheter (400) includes an elongate shaft (402) extending between a proximal end portion (404) (shown schematically) and a distal end (406), and an atraumatic tip (408) arranged at distal end (406). Whereas dilation catheter (300) includes two expandable elements in the form of first and second balloons (310, 312), dilation catheter (400) includes three expandable elements in the form of first, second, and third balloons (410, 412, 414).

Each individual balloon (410, 412, 414) may be generally similar in construction and function to balloons (310, 312) described above. For instance, balloons (410, 412, 414) are suitably sized and mounted to shaft (402) to provide dilation catheter (400) with a maximum outer diameter of less than or equal to approximately 1 millimeter when balloons (410, 412, 414) are in their deflated states shown in FIGS. 10 and 12A-12B. Additionally, balloons (410, 412, 414) are configured to provide dilation catheter (400) with a maximum outer diameter of approximately 6 millimeters or greater when balloons (410, 412, 414) are inflated and aligned longitudinally with one another, as shown in FIG. 12C. Similar to balloons (310, 312), each balloon (410, 412, 414) may include a different reacting agent such as a drug or other chemical. When such a reacting agent is infused through the pores outside of the balloon (410, 412, 414), it can create a reaction at the anatomical targeted tissue that might have been impossible otherwise.

Balloons (410, 412, 414) are slidably coupled with an exterior of shaft (402) via respective elongate balloon support members shown in the form of rails (416, 418, 420). Rails (416, 418, 420) may be similar in construction and function to rails (314, 316) described above. In that regard, as seen in FIG. 11, first rail (416) is defined by a first longitudinal groove (422) formed in a first side portion of shaft (402); second rail (418) is defined by a second longitudinal groove (424) formed in a second side portion of shaft (402); and third rail (420) is defined by a third longitudinal groove (426) formed in a third side portion of shaft (402). Each balloon (410, 412, 414) is configured to slidably translate proximally and distally along its respective rail (416, 418, 420), in response to user input, independently of the other balloons (410, 412, 414). In this manner, balloons (410, 412, 414) translate along respective longitudinal paths that are laterally offset from the central longitudinal axis of shaft (402). Additionally, each balloon (410, 412, 414) may be configured to at least partially collapse within the respective groove (422, 424, 426) when in the unexpanded state so as to minimize the maximum outer diameter of dilation catheter (400) during use, for example during insertion into the ET (26) of a patient.

Balloons (410, 412, 414) and their respective rails (416, 418, 420) of the present example are arranged uniformly about the longitudinal axis of shaft (402) such that no one balloon (410, 412, 414) is directly opposed from any other balloon (410, 412, 414). It will be appreciated, however, that balloons (410, 412, 414) and rails (416, 418, 420) may be provided in various other circumferential arrangements in other examples. Additionally, in some examples balloons (410, 412, 414) may be configured to assume the same maximum size when inflated, while in other examples balloons (410, 412, 414) may be configured to assume different maximum sizes when inflated. In this manner, various quantities and configurations of balloons (410, 412, 414) may be employed while still maintaining a desired maximum outer diameter of dilation catheter (400) when balloons (410, 412, 414) are collectively inflated.

Similar to dilation catheter (300), dilation catheter (400) includes a proximal end portion (404) that provides an inflation port (430, 432, 434) for each of the respective balloons (410, 412, 414), as shown schematically in FIG. 10. First inflation port (430) fluidly communicates with first balloon (410) via a first inflation lumen structure (436) that defines a first inflation lumen (not shown). Second inflation port (432) fluidly communicates with second balloon (412) via a second inflation lumen structure (438) that defines a second inflation lumen (not shown). Third inflation port (434) fluidly communicates with third balloon (414) via a third inflation lumen structure (440) that defines a third inflation lumen (not shown). Each inflation port (430, 432, 434) and its respective inflation lumen structure (436, 438, 440) may be generally similar to inflation lumen ports (322, 324) and inflation lumen structures (326, 328) described above. Proximal end portion (404) of dilation catheter (400) further includes a plurality of balloon actuators (442, 446, 450) similar to balloon actuators (330, 334) and operable to provide independent longitudinal actuation of each balloon (410, 412, 414) relative to shaft (402). Similar to the configuration of dilation catheter (300) described above, first actuator (442) of dilation catheter (400) is operatively coupled with first balloon (410) via a first linkage (444); second actuator (446) is operatively coupled with second balloon (412) via a second linkage (448); and third actuator (450) is operatively coupled with third balloon (414) via a third linkage (452).

Figure 12A:
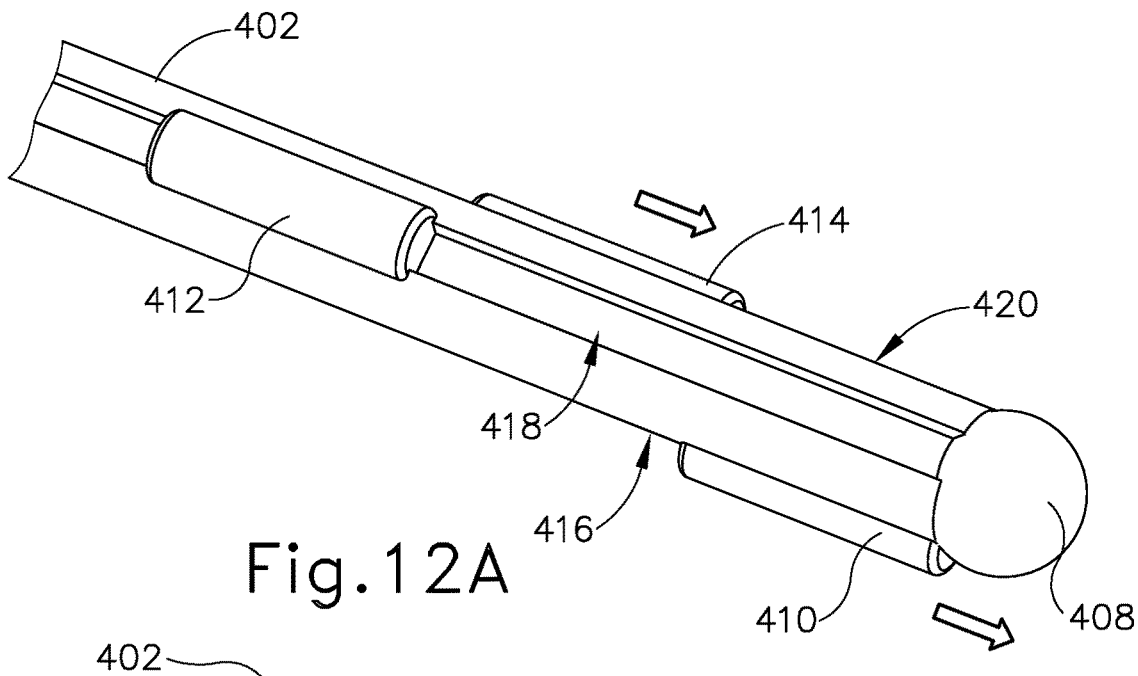
FIG. 12A depicts a perspective view of a distal portion of the balloon dilation catheter of FIG. 11, showing the first balloon in a distal position, the second balloon in a proximal position, and the third balloon in a medial position, with all balloons being in a deflated state.
Figure 12B:
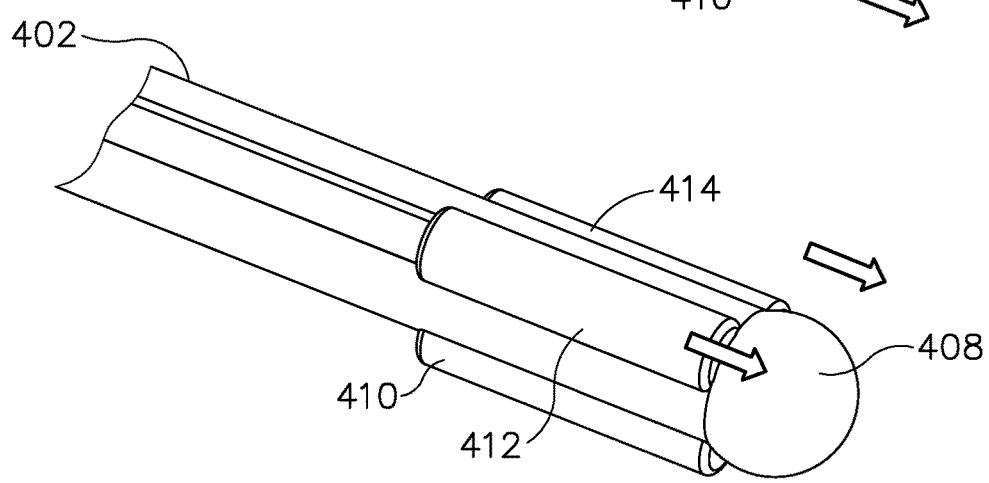
FIG. 12B depicts a perspective view of a distal portion of the balloon dilation catheter of FIG. 11, showing all three balloons in their distal positions and deflated.
Figure 12C:
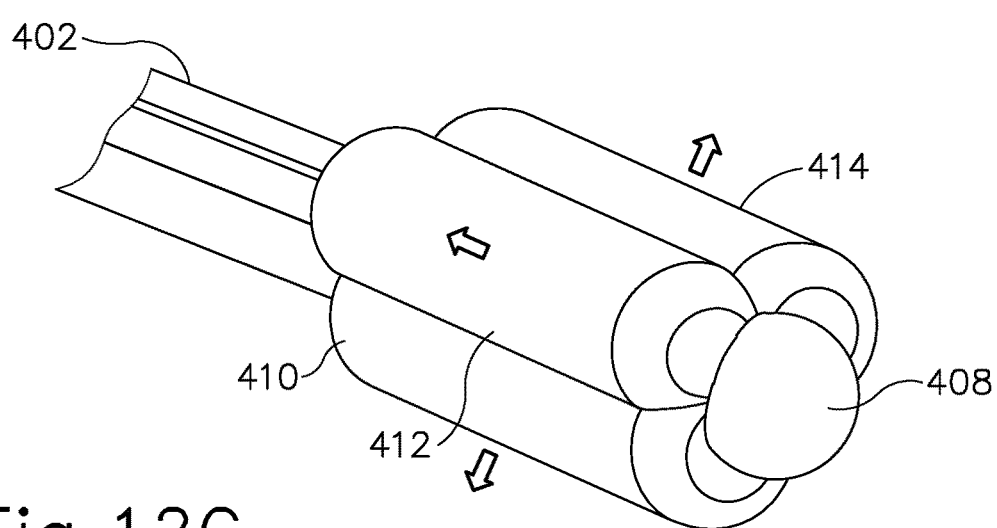
FIG. 12C depicts a perspective view of a distal portion of the balloon dilation catheter of FIG. 11, showing all three balloons in an inflated state.

As shown in FIGS. 10 and 12A-12C, balloons (410, 412, 414) of dilation catheter (400) may be advanced independently and sequentially along shaft (402) during use, in a manner similar to balloons (310, 312) of dilation catheter (300). FIG. 10 shows balloons (410, 412, 414) deflated and in exemplary proximal positions in which balloons (410, 412, 414) are spaced proximally from distal end (406) of shaft (402). FIG. 12A shows first balloon (410) in a distal position, second balloon (412) in a proximal position, and third balloon (414) in the medial position. FIG. 12B shows all three balloons (410, 412, 414) advanced to their distal positions in which distal ends of balloons (410, 412, 414) confront a proximal surface of distal tip (308). After being advanced to their distal positions, balloons (410, 412, 414) may be inflated to dilate an anatomical passageway in which balloons (410, 412, 414) are positioned, such as the ET (26) of a patient. As described above, balloons (410, 412, 414) of the present example are suitably sized and arranged to provide dilation catheter (400) with a maximum outer diameter of at least 6 millimeters when balloons (410, 412, 414) are inflated in their distal positions. When deflated, balloons (410, 412, 414) are configured to provide dilation catheter (400) with a maximum outer diameter of less than or equal to approximately 1 millimeter. It will be appreciated, however, that balloons (410, 412, 414) may be provided with various other sizes in other examples.

Dilation catheters (300, 400) shown and described herein may be further configured in accordance with one or more teachings of U.S. Pat. No. 10,070,993, entitled "System and Method for Treatment of Eustachian Tube from Middle Ear Approach," issued on Sep. 11, 2018, the disclosure of which is incorporated by reference herein.

III. Exemplary Method of Dilating Eustachian Tube with Dilation Catheter Having Multiple Balloons FIGS. 13A-14C show an exemplary method of dilating the ET (26) of a patient using dilation catheter (300) described above. It will be appreciated that a similar method may be performed using dilation catheter (400). Rather than advancing balloon catheter (400) through a nostril, into the nasal cavity, and through the pharyngeal ostium (28), the method shown includes accessing the ET (26) through the ear canal (20) and the tympanic membrane (22). In use, balloon dilation catheter (300) is advanced through the ear canal (20), for instance under visual guidance using an endoscope (60). In some examples, a guide catheter may be used to aid in accessing the ET (26) with balloon catheter (300) through the ear canal (20). In addition, or in the alternative, a guiding element such as a guidewire or illuminating fiber (not shown) may be used to aid in accessing the ET (26). Of course, such guidance features are merely optional. It should therefore be understood that balloon catheter (300) may be used to access the ET (26) via the ear canal (20) and dilate the ET (26) without the use of an additional guide catheter or guidewire, etc.

Those of ordinary skill in the art will recognize that the tympanic membrane (22) provides a physical barrier to passage of an instrument such as balloon catheter (400) from the ear canal (20) into the ET (26). Thus, an operator must somehow address the presence of the tympanic membrane (22) in order to gain access to the ET (26) from the ear canal (20). The following description provides a merely illustrative method for handling the tympanic membrane (22) in order to suitably insert balloon catheter (300) into the ET (26) via the ear canal (20). Other illustrative methods are disclosed in U.S. Pat. No. 10,070,993, entitled "System and Method for Treatment of Eustachian Tube from Middle Ear Approach," incorporated by reference above.

In the example shown in FIGS. 13A-14C, the operator accesses the middle ear (14) and ET (26) without compromising the integrity of the tympanic membrane (22). As shown in FIG. 14A, the operator makes an incision along line (502) in the tissue surrounding tympanic membrane (22) but does not cut any part of tympanic membrane (22) itself. In the present example, cut line (502) is made adjacent to an inferior aspect of the tympanic membrane (22), along approximately half the perimeter of the tympanic membrane (22). Particularly, cut line (502) extends from an inferior-posterior aspect of the tympanic membrane (22) to an inferior-anterior aspect of the tympanic membrane (22). Cut line (502) may be formed using any suitable conventional instrumentation.

In other examples, cut line (502) may be made along a different aspect of the tympanic membrane (22). For example, in alternative methods cut line (502) may be made from a superior-posterior aspect of the tympanic membrane (22) to a superior-anterior aspect. Moreover, cut line (502) may be made such that it extends along a different portion of the tympanic membrane (22) and may include a different length or shape than that shown. Other suitable positioning and configurations of cut line (502) that may be made in order to create a sufficient opening (504) for access to the middle ear (14) and ET (26) will be apparent to persons skilled in the art in view of the teachings herein. It will be understood that cut line (502) may be made by commencing the cut at any point along cut line (502).

Cutting along approximately half the perimeter of the tympanic membrane (22) enables the operator to displace approximately half of the tympanic membrane (22) by folding the tympanic membrane (22). In particular, as shown in FIGS. 13A-13C and 14B, cut line (502) forms a flap (506) that may be folded superiorly such that an opening (504) is created that provides access to the middle ear (14) and ET (26). Of course, depending on where cut line (502) is made along a different portion of tympanic membrane (22), flap (506) may be folded in a different manner or direction in order to create an opening with access to the middle ear (14) and ET (26). In some examples, if cut line (502) is made from a superior-posterior aspect of the tympanic membrane (22) to a superior-anterior aspect, flap (506) of severed tissue and tympanic membrane (22) may be folded in the inferior direction. Other folding configurations and directions will be apparent to persons skilled in the art in view of the teachings herein.

As shown in FIG. 14B, the operator fixes flap (506) using a suture (510). In particular, the operator sutures the severed tissue portion of flap (508) to a superior portion of the ear canal (20), such as tissue adjacent to a superior portion of tympanic membrane (22). In order to protect the integrity of the tympanic membrane (22), the operator does not puncture or otherwise compromise the tympanic membrane (22) with a needle when implanting suture (510) on flap (508). In some other examples, the operator may affix the flap (508) in a folded configuration in a different manner, such as by adhesive, or in any other suitable manner as will be apparent to persons skilled in the art in view of the teachings herein.

Figure 13A:
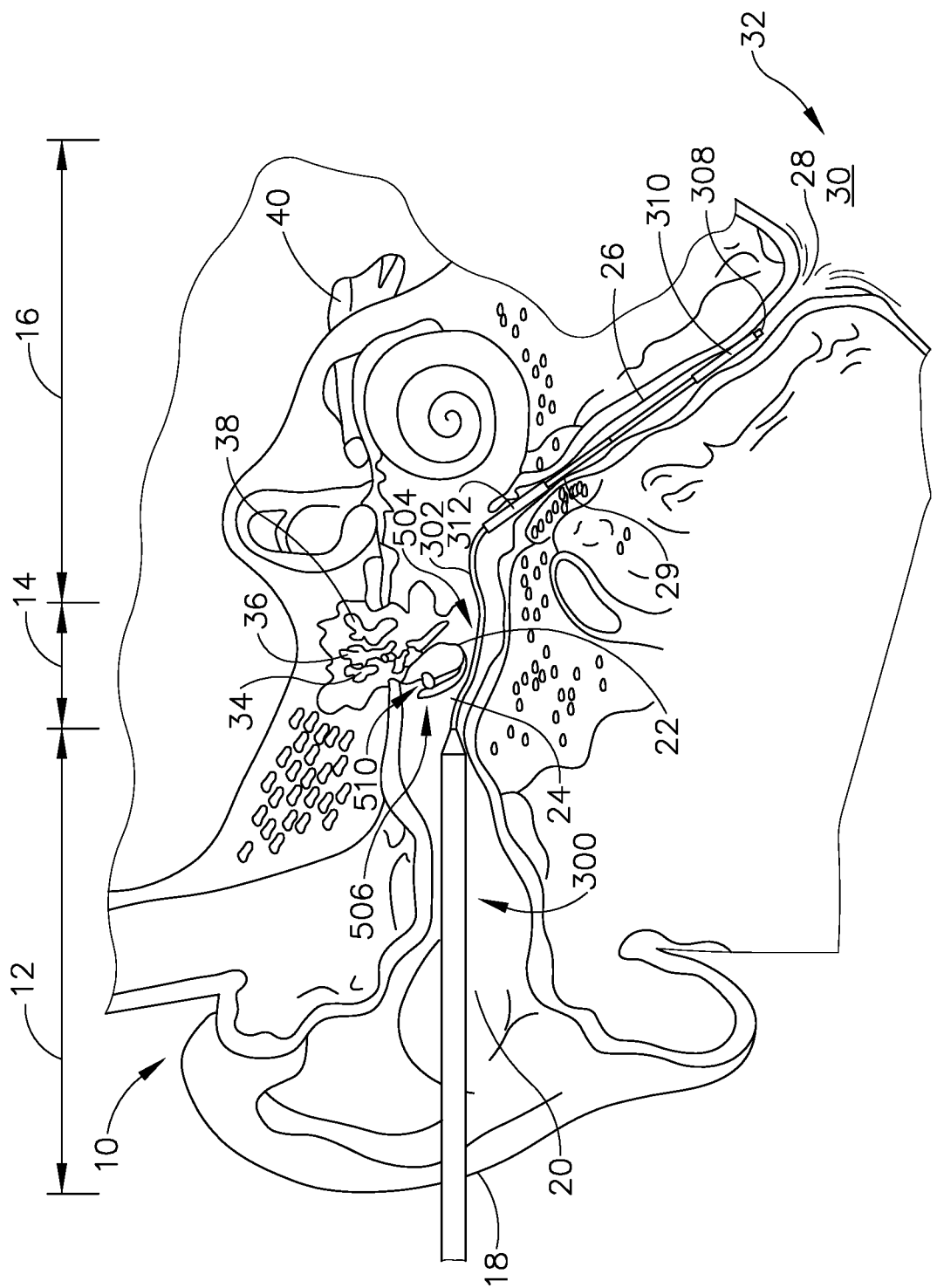
FIG. 13A depicts a cross-sectional view of a patient's head, showing a distal portion of the balloon dilation catheter of FIG. 7 positioned within the patient's Eustachian tube, with the first balloon deflated in its distal position and inside of the Eustachian tube and with the second balloon deflated in its proximal position and outside of the Eustachian tube.

As shown in FIG. 13A, once a sufficient opening (504) is created, an operator may direct a distal end portion of balloon dilation catheter (300) into the ear canal (20), through opening (504), through the middle ear (14), past the isthmus (29), and into the ET (26). Before advancing the distal end portion of dilation catheter (400) into the ET (26), both balloons (310, 312) are fully deflated and first balloon (310) is actuated to its distal position while second balloon (312) is maintained in its proximal position, such that balloons (310, 312) are longitudinally spaced from one another. Accordingly, during the initial step of inserting the distal end portion of dilation catheter into the ET (26) as shown in FIG. 13A, only first balloon (310) passes into the ET (26) while second balloon (312) remains at least partially outside of the ET (26), proximally of isthmus (29). Positioning balloons (310, 312) in such an arrangement provides dilation catheter (300) with the smallest possible outer diameter, of approximately 1 millimeter or less as described above, and thereby minimizes disruption to isthmus (29) and adjacent components of inner ear (16) during the insertion step shown in FIG. 13A. As described above, deflated balloons (310, 312) are configured to collapse at least partially into longitudinal grooves (318, 320) of their respective rails (314, 316) to further promote a minimized outer diameter of dilation catheter (300) during insertion into the ET (26).

Figure 13B:
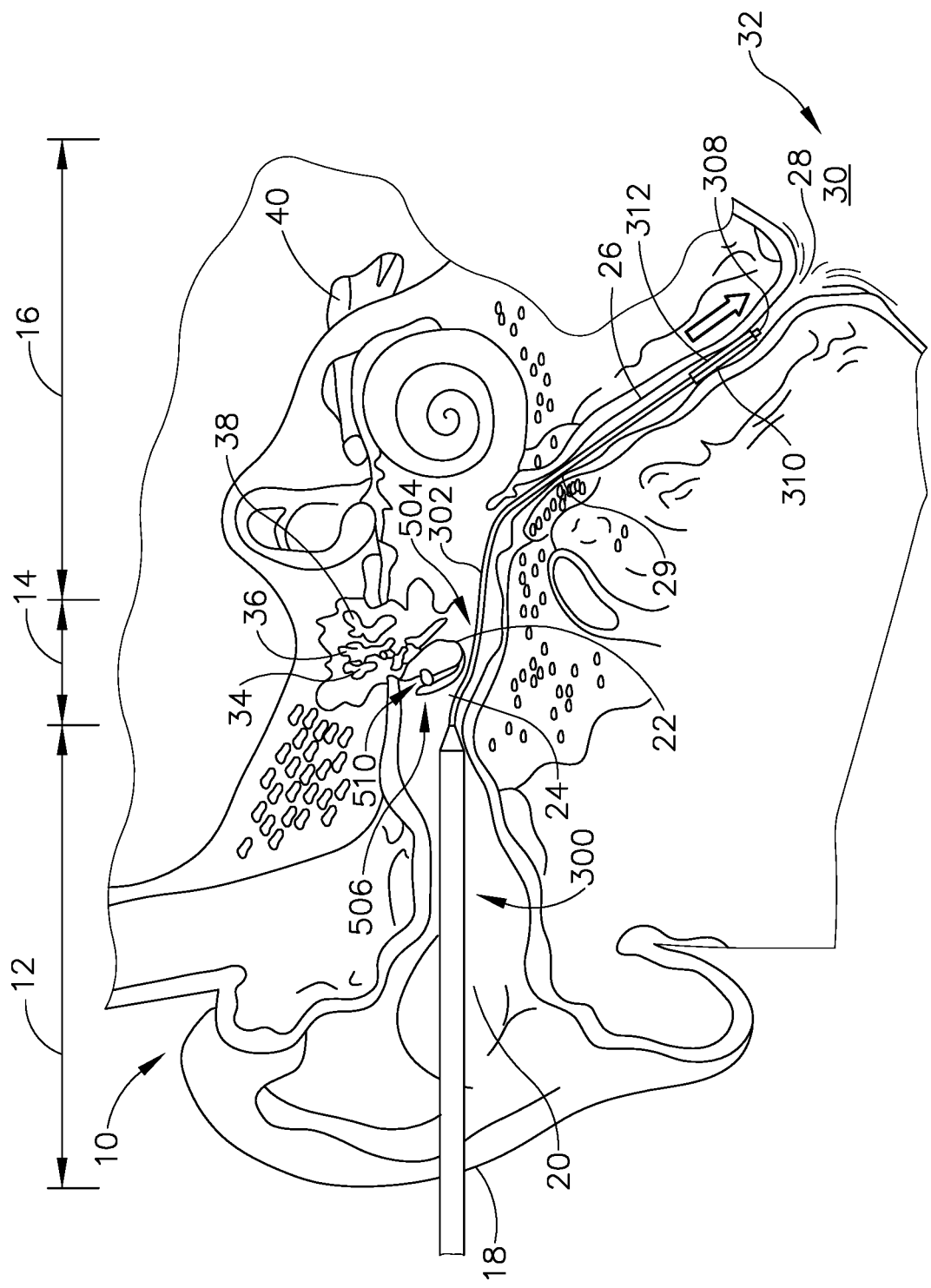
FIG. 13B depicts a cross-sectional view of the patient's head of FIG. 13A, showing the second balloon of the balloon dilation catheter advanced to its distal position within the Eustachian tube, with both balloons of the dilation catheter remaining in their deflated state.
Figure 13C:
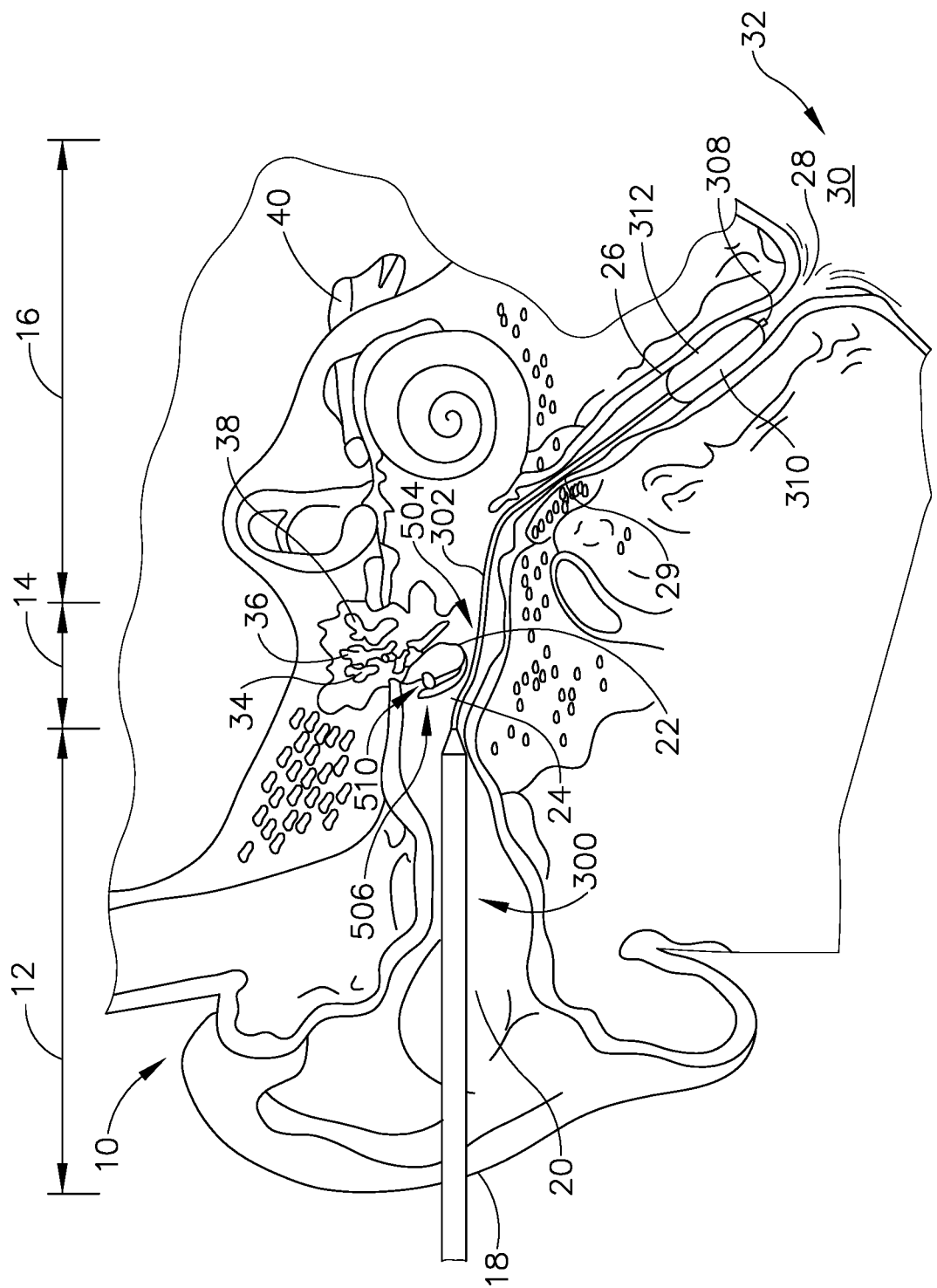
FIG. 13C depicts a cross-sectional view of the patient's head of FIG. 13B, showing the balloons inflated to thereby dilate the Eustachian tube.

As shown in FIG. 13B, following placement of first balloon (310) within the ET (26), second balloon (312) is actuated to its distal position to thereby advance second balloon (312) into the ET (26) in alignment with first balloon (310), both of which remain deflated. As shown in FIG. 13C, once balloons (310, 312) are suitably positioned within the ET (26), the operator inflates both balloons (310, 312) to thereby dilate the ET (26). As described above, in some examples balloons (310, 312) may be configured to cooperate to provide dilation catheter (300) with a maximum outer diameter of approximately 6 millimeters or more to provide a desired degree of ET dilation. Once inflated, balloons (310, 312) may then be held in place within the ET (26) for an extended period of time (e.g. several seconds or minutes). In some instances, the operator may wish to repeatedly inflate and deflate balloons (310, 312) within the ET (26) to achieve a desired dilation effect. Balloon catheter (300) may also deliver a substance to the ET (26), such as one or more of the therapeutic or diagnostic agents described herein. In some examples, balloons (310, 312) may cooperate to carry an expandable stent for delivery into the ET (26) upon expansion of balloons (310, 312).

Once the ET (26) has been suitably dilated, balloons (310, 312) may be deflated and balloons (310, 312) may be withdrawn from the ET (26) by reversing the insertion steps described above. For instance, first or second balloon (310, 312) may be retracted to its proximal position and thereby withdrawn from the ET (26) while the other balloon (310, 312) remains within the ET (26) in its distal position. Then, balloon catheter (300) as a whole may be withdrawn from the patient, thereby withdrawing the other deflated balloon (310, 312) from the ET (26). Following removal of balloon dilation catheter (300), the ET (26) is left dilated and able to resume normal functioning.

Following removal of balloon catheter (300) from the patient, the operator may replace flap (506) as generally shown in FIG. 14C. In the present example, the operator severs, decouples, or otherwise removes suture (510) and causes flap (506) to return to the inferior position adjacent to cut line (502). Then, the operator couples the flap (506) with the tissue adjacent to cut line (502), for example with an adhesive. Suitable surgical adhesives will be apparent to persons skilled in the art in view of the teachings herein. In other examples, the operator may couple the flap (506) to the tissue adjacent to cut line (502) in some other fashion, such as via suturing. Other suitable techniques that may be used to couple the flap (506) to the tissue adjacent to cut line (502) will be apparent to persons skilled in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A dilation catheter comprising: (a) a shaft; (b) a tip at a distal end of the shaft, wherein the tip is sized and configured to pass through an isthmus of a Eustachian tube (ET); and (c) an expandable element moveably coupled with the shaft, wherein the expandable element is moveable along an exterior of the shaft between a proximal position and a distal position, wherein the expandable element is operable to transition between an unexpanded state and an expanded state, wherein the expandable element in the unexpanded state is configured for insertion into the ET via the isthmus, wherein the expandable element in the expanded state is configured to dilate the ET.

Example 2

The dilation catheter of Example 1, wherein the expandable element comprises a balloon.

Example 3

The dilation catheter of any of the previous Examples, wherein the expandable element is movable along a path that is laterally offset from a central axis of the shaft.

Example 4

The dilation catheter of any of the previous Examples, further comprising an actuator, wherein the actuator is operable to actuate the expandable element between the proximal position and the distal position.

Example 5

The dilation catheter of any of the previous Examples, wherein the expandable element is configured to provide the dilation catheter with a maximum outer diameter of less than or equal to 1 millimeter when the expandable element is in the unexpanded state.

Example 6

The dilation catheter of any of the previous Examples, wherein the expandable element comprises a first expandable element, wherein the dilation catheter further comprises a second expandable element movably coupled with the shaft, wherein the second expandable is movable along the shaft between a proximal position and a distal position, wherein the second expandable element is operable to transition between an unexpanded state and an expanded state.

Example 7

The dilation catheter of Example 6, wherein the first and second expandable elements are movable along the shaft independently of one another.

Example 8

The dilation catheter of any of Examples 6 through 7, further comprising: (a) a first actuator operable to move the first expandable element along the shaft; and (b) a second actuator operable to move the second expandable element along the shaft.

Example 9

The dilation catheter of any of Examples 6 through 8, further comprising: (a) a first elongate member extending along a first side of the shaft, wherein the first expandable element is movable between the proximal and distal positions along the first elongate member; and (b) a second elongate member extending along a second side of the shaft, wherein the second expandable element is movable between the proximal and distal positions along the second elongate member.

Example 10

The dilation catheter of any of Examples 6 through 9, wherein the first and second expandable elements are operable to transition between the unexpanded states and the expanded states independently of one another.

Example 11

The dilation catheter of any of Examples 6 through 10, further comprising: (a) a first inflation lumen in fluid communication with the first expandable element; and (b) a second inflation lumen in fluid communication with the second expandable element, wherein the first and second inflation lumens extend longitudinally through the shaft.

Example 12

The dilation catheter of any of Examples 6 through 11, wherein the first and second expandable elements are configured to cooperate to provide the dilation catheter with a maximum outer diameter of at least 6 millimeters when the first and second expandable elements are in the expanded states.

Example 13

The dilation catheter of any of Examples 6 through 12, wherein the first and second expandable elements are configured to be positioned along the shaft so as to provide the dilation catheter with a maximum outer diameter of less than or equal to 1 millimeter when the first and second expandable elements are in the unexpanded states.

Example 14

The dilation catheter of any of Examples 6 through 13, wherein the first and second expandable elements are positionable so as to be opposed from one another about a longitudinal axis of the shaft when the first and second expandable elements are in the distal positions.

Example 15

The dilation catheter of any of Examples 6 through 14, further comprising a third expandable element movably coupled with the shaft, wherein the third expandable is movable along the shaft between a proximal position and a distal position independently of the first and second expandable elements, wherein the third expandable element is operable to transition between an unexpanded state and an expanded state.

Example 16

A dilation catheter comprising: (a) a shaft; (b) a first expandable element moveably coupled with the shaft, wherein the first expandable element is moveable along the shaft between a first position and a second position; and (c) a second expandable element moveably coupled with the shaft, wherein the second expandable element is movable along the shaft between a first position and a second position, wherein each of the first and second expandable elements is operable to transition between an unexpanded state and an expanded state, wherein each of the first and second expandable elements is configured to pass through an isthmus of a Eustachian tube (ET) in the unexpanded state, wherein the first and second expandable elements are configured to cooperate to dilate the ET when in the expanded states.

Example 17

The dilation catheter of Example 16, wherein the first and second expandable elements are operable to move along the shaft independently of one another.

Example 18

The dilation catheter of any of Examples, wherein the first and second expandable elements are operable transition between the unexpanded states and the expanded states independently of one another.

Example 19

A method of dilating a Eustachian tube (ET) of a patient using a dilation catheter having a shaft and an expandable element, wherein the expandable element is movable along the shaft between a proximal position and a distal position, wherein the method comprises: (a) forming an opening in or adjacent to a tympanic membrane of the patient; (b) directing a distal end of the dilation catheter into an ear canal of the patient with the expandable element in the proximal position; (c) with the expandable element remaining in the proximal position, advancing the distal end of the dilation catheter: (i) through the formed opening, (ii) through a middle ear of the patient, (iii) through an isthmus between the middle ear and the ET, and (iv) into the ET such that at least a portion of the expandable element remains outside of the ET; (d) actuating the expandable element along the dilation catheter from the proximal position to the distal position to thereby advance the expandable element into the ET; and (e) with the expandable element in the distal position, expanding the expandable element to thereby dilate the ET.

Example 20

The dilation catheter of Example 19, wherein the expandable element comprises a first expandable element, wherein the dilation catheter further comprises a second expandable element movable along the shaft between a proximal position and a distal position, wherein advancing the distal end of the dilation catheter into the ET comprises advancing the second expandable element into the ET while at least a portion of the first expandable element remains outside of the ET, wherein the method further comprises expanding the second expandable element to thereby dilate the ET.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A dilation catheter comprising:
   (a) a shaft extending along a central longitudinal axis;
   (b) a tip at a distal end of the shaft, wherein the tip is sized and configured to pass through an isthmus of a Eustachian tube (ET); and
   (c) first and second expandable elements moveably coupled with the shaft, wherein a center of the first expandable element extends along a first longitudinal axis, wherein a center of the second expandable element extends along a second longitudinal axis, wherein the first and second expandable elements are independently moveable along an exterior surface of the shaft between a proximal position and a distal position, wherein the first and second expandable elements are operable to transition between an unexpanded state and an expanded state, wherein the first and second longitudinal axes of the first and second expandable elements are laterally offset from the central longitudinal axis of the shaft,
   wherein the first and second expandable elements in the unexpanded state are configured for insertion into the ET via the isthmus, wherein the first and second expandable elements in the expanded state are configured to dilate the ET.

2. The dilation catheter of claim 1, wherein the first expandable element comprises a first dilation balloon.

3. The dilation catheter of claim 1, wherein the first expandable element is configured to provide the dilation catheter with a maximum outer diameter of less than or equal to 1 millimeter when the first expandable element is in the unexpanded state.

4. The dilation catheter of claim 1, further comprising: (a) a first actuator operable to move the first expandable element along the shaft; and (b) a second actuator operable to move the second expandable element along the shaft.

5. The dilation catheter of claim 1, further comprising: (a) a first elongate member extending along a first side of the shaft, wherein the first expandable element is moveable between the proximal and distal positions along the first elongate member; and (b) a second elongate member extending along a second side of the shaft, wherein the second expandable element is moveable between the proximal and distal positions along the second elongate member.

6. The dilation catheter of claim 1, further comprising: (a) a first inflation lumen in fluid communication with the first expandable element; and (b) a second inflation lumen in fluid communication with the second expandable element, wherein the first and second inflation lumens extend longitudinally through the shaft.

7. The dilation catheter of claim 1, wherein the first and second expandable elements are configured to cooperate to provide the dilation catheter with a maximum outer diameter of at least 6 millimeters when the first and second expandable elements are in the expanded states.

8. The dilation catheter of claim 1, wherein the first and second expandable elements are configured to be positioned along the shaft so as to provide the dilation catheter with a maximum outer diameter of less than or equal to 1 millimeter when the first and second expandable elements are in the unexpanded states.

9. The dilation catheter of claim 1, wherein the first and second expandable elements are positionable so as to be opposed from one another about the central longitudinal axis of the shaft when the first and second expandable elements are in the distal positions.

10. The dilation catheter of claim 1, further comprising a third expandable element moveably coupled with the shaft, wherein the third expandable element is moveable along the shaft between a proximal position and a distal position independently of the first and second expandable elements, wherein the third expandable element is operable to transition between an unexpanded state and an expanded state.

11. The dilation catheter of claim 1, wherein the shaft has a maximum perimeter, wherein the first and second expandable elements are configured to extend outside of the maximum perimeter in both the unexpanded and expanded states.

12. The dilation catheter of claim 1, wherein the shaft includes first and second longitudinally extending rails, wherein the first expandable element is configured to slide along the exterior surface of the shaft and at least partially fit within the first longitudinally extending rail, wherein the second expandable element is configured to slide along the exterior surface of the shaft and at least partially fit within the second longitudinally extending rail.

13. The dilation catheter of claim 1, wherein the shaft has a maximum perimeter, wherein the first and second expandable elements are configured to extend outside of the maximum perimeter in both the unexpanded and expanded states.

14. The dilation catheter of claim 1, wherein the wherein the first and second expandable elements each extend parallel to the central longitudinal axis of the shaft.

15. A dilation catheter comprising:
(a) a first actuator;
(b) a second actuator;
(c) a shaft extending along a first longitudinal axis, wherein the shaft includes an exterior surface;
(d) a first expandable element coupled with the first actuator, wherein the first actuator is operable to drive translation of the first expandable element along the exterior surface of the shaft between a first position and a second position, wherein the first expandable element extends along a second longitudinal axis; and
(e) a second expandable element coupled with the second actuator, wherein the second actuator is operable to drive translation of the second expandable element along the exterior surface of the shaft between a first position and a second position, wherein the second expandable element extends along a third longitudinal axis, wherein the second and third longitudinal axes are each laterally offset from the first longitudinal axis,
wherein each of the first and second expandable elements is operable to transition between an unexpanded state and an expanded state,
wherein each of the first and second expandable elements is configured to pass through an isthmus of a Eustachian tube (ET) in the unexpanded state,
wherein the first and second expandable elements are configured to cooperate to dilate the ET when in the expanded states,
wherein the first and second expandable elements are translatable along the exterior surface of the shaft independently of one another.

16. The dilation catheter of claim 15, further comprising a third expandable element moveably coupled with the shaft, wherein the third expandable element is moveable along the shaft between a proximal position and a distal position, wherein the third expandable element is operable to transition between an unexpanded state and an expanded state.

17. The dilation catheter of claim 15, wherein the shaft includes first and second longitudinally extending rails, wherein the first expandable element is configured to slide along the exterior surface of the shaft and at least partially fit within the first longitudinally extending rail, wherein the second expandable element is configured to slide along the exterior surface of the shaft and at least partially fit within the second longitudinally extending rail.

18. A dilation catheter comprising:
(a) a shaft that includes an exterior;
(b) a first expandable element in direct contact with the exterior of the shaft, wherein the first expandable element is translatable along the exterior of the shaft between a proximal position and a distal position, wherein the first expandable element is operable to transition between an unexpanded state and an expanded state, wherein the first expandable element in the unexpanded state is configured is sized and configured to pass through an isthmus of a Eustachian tube (ET), wherein the first expandable element in the expanded state is configured to dilate the ET, wherein the first expandable element extends around only a portion of the circumference of the shaft in the unexpanded and expanded states; and
(c) second and third expandable elements that are translatable along the shaft between proximal positions and distal positions, wherein the second and third expandable elements are operable to transition between an unexpanded state and an expanded state.

19. The dilation catheter of claim 18, wherein the shaft extends along a central longitudinal axis, wherein a center of the first expandable element extends along a first longitudinal axis, wherein the longitudinal axis of the first expandable element is laterally offset from the central longitudinal axis of the shaft.

20. The dilation catheter of claim 18, wherein the shaft has a maximum perimeter, wherein the first expandable element is configured to extend outside of the maximum perimeter in both the unexpanded and expanded states.

* * * * *